United States Patent
Liu et al.

(10) Patent No.: US 11,753,388 B2
(45) Date of Patent: Sep. 12, 2023

(54) COMPOSITION FOR INHIBITING ALPHA-GLUCOSIDASE AND APPLICATION THEREOF

(71) Applicant: ZHENGZHOU FRUIT RESEARCH INSTITUTE, CHINESE ACADEMY OF AGRICULTURAL SCIENCES, Zhengzhou (CN)

(72) Inventors: Jiechao Liu, Zhengzhou (CN); Qiang Zhang, Zhengzhou (CN); Zhonggao Jiao, Zhengzhou (CN); Dalei Chen, Zhengzhou (CN); Junkun Pan, Zhengzhou (CN); Chunling Zhang, Zhengzhou (CN); Hui Liu, Zhengzhou (CN); Wenbo Yang, Zhengzhou (CN); Zhenzhen Lv, Zhengzhou (CN)

(73) Assignee: ZHENGZHOU FRUIT RESEARCH INSTITUTE, CHINESE ACADEMY OF AGRICULTURAL SCIENCES, Henan (CN)

(*) Notice: Subject to any disclaimer, the term of this patent is extended or adjusted under 35 U.S.C. 154(b) by 0 days.

(21) Appl. No.: 18/081,979

(22) Filed: Dec. 15, 2022

(65) Prior Publication Data

US 2023/0129488 A1 Apr. 27, 2023

Related U.S. Application Data

(63) Continuation of application No. PCT/CN2022/111359, filed on Aug. 10, 2022.

(30) Foreign Application Priority Data

Aug. 20, 2021 (CN) .......................... 202110962157.2

(51) Int. Cl.
  *C07D 311/04* (2006.01)
  *A61K 9/00* (2006.01)
  *A61K 9/16* (2006.01)

(52) U.S. Cl.
  CPC .......... *C07D 311/04* (2013.01); *A61K 9/0056* (2013.01); *A61K 9/16* (2013.01)

(58) Field of Classification Search
  CPC .. A61K 2300/00; A61K 8/9789; A61K 45/06; A61K 36/48; A61K 9/0014; A61K 31/352; A61K 31/353; A61K 8/498; A61K 8/347; A61K 8/35; A61K 36/28; A61K 36/185; A61K 8/9794; A61K 8/671; A61K 2800/782; A61K 8/37; A61K 2800/412; A61K 2800/5922; A61K 31/12; A61K 31/7048; A61K 8/41; A61K 31/35; A61K 36/87; A61K 8/0208; A61K 2800/522; A61K 31/192; A61K 8/0212; A61K 8/345; A61K 8/64; A61K 31/355; A61K 8/0241; A61K 8/40; A61K 31/198; A61K 31/404; A61K 31/05; A61K 8/8152; A61K 31/47; A61K 8/06; A61K 8/731; A61K 9/0053; A61K 36/82; A61K 31/4745; A61K 8/361; A61K 8/44; A61K 8/0245; A61K 8/062; A61K 8/492; A61K 8/4973; A61K 31/122; A61K 33/04; A61K 8/19; A61K 8/27; A61K 8/29; A61K 8/891; A61K 8/9728; A61K 2800/51; A61K 33/00; A61K 8/34; A61K 8/922; A61K 2800/524; A61K 33/06; A61K 47/10; A61K 8/36; A61K 8/368; A61K 8/60; A61K 2800/594; A61K 31/00; A61K 31/40; A61K 31/405; A61K 31/455; A61K 33/24; A61K 36/06; A61K 36/484; A61K 36/488; A61K 8/46; A61K 8/8147; A61K 2800/48; A61K 2800/70; A61K 31/07; A61K 31/132; A61K 31/133; A61K 31/60; A61K 36/45; A61K 36/889; A61K 8/025; A61K 8/365; A61K 8/42; A61K 8/645; A61K 8/86; A61K 8/895; A61K 2800/242; A61K 2800/56; A61K 2800/60; A61K 31/19; A61K 31/55; A61K 31/565;
(Continued)

(56) References Cited

U.S. PATENT DOCUMENTS 6,455,057 B1 * 9/2002 Barrett .................. A61K 8/361
  514/844
2003/0078231 A1 4/2003 Wilburn

FOREIGN PATENT DOCUMENTS

CN 20160052106 A 5/2016
CN 108578279 A 9/2018
(Continued)

OTHER PUBLICATIONS

CN111388461A, Jul. 10, 2020 translation (Year: 2020).*
(Continued)

*Primary Examiner* — Audrea B Coniglio
(74) *Attorney, Agent, or Firm* — SZDC Law PC

(57) ABSTRACT

The present invention discloses a composition for inhibiting α-glucosidase and application thereof, and belongs to the technical field of natural active compounds. The composition of the present invention contains daidzein and quercetin derivatives, and the quercetin derivative is taxifolin or 3-O-methyl quercetin, where the mass ratio of the daidzein to the taxifolin is 8:25-10:25; and the mass ratio of the daidzein to the 3-O-methyl quercetin is 8:2-8:4. The composition of the present invention has an obvious synergistic effect of inhibiting α-glucosidase, and the effect thereof is better than that of using the flavonoid compound alone, and may reduce a dosage of the use of drugs and occurrence of drug resistance.

8 Claims, 14 Drawing Sheets

(58) Field of Classification Search
CPC .. A61K 36/064; A61K 36/736; A61K 36/752; A61K 8/027; A61K 8/0279; A61K 8/24; A61K 8/375; A61K 8/494; A61K 8/732; A61K 8/92; A61K 2800/85; A61K 31/20; A61K 31/34; A61K 31/375; A61K 31/522; A61K 31/56; A61K 33/14; A61K 38/168; A61K 8/11; A61K 8/735; A61K 9/0019; A61K 9/0095; A61K 9/06; A61K 2800/596; A61K 2800/88; A61K 31/13; A61K 31/568; A61K 31/7004; A61K 35/744; A61K 36/04; A61K 36/8967; A61K 36/9066; A61K 36/9068; A61K 8/447; A61K 8/676; A61K 8/88; A61K 8/9717; A61K 2800/624; A61K 2800/87; A61K 31/047; A61K 31/194; A61K 31/197; A61K 31/277; A61K 31/4439; A61K 31/57; A61K 31/7076; A61K 33/242; A61K 33/30; A61K 35/74; A61K 35/747; A61K 36/22; A61K 36/47; A61K 36/53; A61K 36/60; A61K 38/4873; A61K 31/28; A61K 31/728; A61K 47/02; A61K 47/32; A61K 47/44; A61K 47/46; A61K 8/26; A61K 8/31; A61K 8/49; A61K 8/585; A61K 8/678; A61K 8/87; A61K 8/99; A61K 9/1075; A61K 9/70; A61K 9/7007; A61K 9/7092; A61K 2800/74; A61K 2800/805; A61K 31/135; A61K 31/167; A61K 31/381; A61K 31/44; A61K 31/445; A61K 31/485; A61K 31/4965; A61K 31/5685; A61K 31/569; A61K 33/32; A61K 33/34; A61K 36/23; A61K 36/55; A61K 36/68; A61K 36/899; A61K 38/00; A61K 38/28; A61K 8/22; A61K 8/466; A61K 8/4926; A61K 8/72; A61K 8/8176; A61K 8/894; A61K 9/0021; A61K 2800/31; A61K 2800/438; A61K 31/01; A61K 31/065; A61K 31/385; A61K 31/426; A61K 31/7024; A61K 31/711; A61K 31/713; A61K 33/08; A61K 36/00; A61K 36/15; A61K 36/16; A61K 36/282; A61K 36/286; A61K 36/31; A61K 36/67; A61K 36/73; A61K 36/77; A61K 36/886; A61K 38/08; A61K 38/1709; A61K 38/1774; A61K 38/43; A61K 38/45; A61K 38/465; A61K 39/39558; A61K 47/06; A61K 47/08; A61K 47/22; A61K 47/26; A61K 47/34; A61K 47/38; A61K 48/00; A61K 48/005; A61K 8/0216; A61K 8/046; A61K 8/20; A61K 8/39; A61K 8/415; A61K 8/602; A61K 8/73; A61K 8/736; A61K 8/8158; A61K 8/9761; A61K 8/9771; A61K 9/00; A61K 9/0009; A61K 9/0034; A61K 9/08; A61K 9/107; A61K 9/1273; A61K 9/16; A61K 9/2013; A61K 9/2054; A61K 9/48; A61K 9/4858; A61K 9/5176; A61K 9/5192; A61K 9/703; A61K 2800/10; A61K 2800/262; A61K 2800/434; A61K 2800/622; A61K 2800/81; A61K 2800/92; A61K 31/015; A61K 31/095; A61K 31/121; A61K 31/136; A61K 31/155; A61K 31/17; A61K 31/202; A61K 31/327; A61K 31/41; A61K 31/4164; A61K 31/433; A61K 31/437; A61K 31/473; A61K 31/517; A61K 31/675; A61K 31/7032; A61K 33/28; A61K 36/062; A61K 36/52; A61K 36/54; A61K 36/61; A61K 36/76; A61K 38/1767; A61K 38/48; A61K 38/482; A61K 38/488; A61K 38/4886; A61K 8/02; A61K 8/044; A61K 8/064; A61K 8/23; A61K 8/25; A61K 8/4913; A61K 8/4966; A61K 8/8129; A61K 8/8182; A61K 8/9767; A61K 9/145; A61K 2236/00; A61K 2800/30; A61K 2800/413; A61K 2800/47; A61K 2800/52; A61K 2800/546; A61K 2800/592; A61K 2800/75; A61K 2800/82; A61K 2800/83; A61K 2800/91; A61K 31/075; A61K 31/085; A61K 31/195; A61K 31/337; A61K 31/357; A61K 31/36; A61K 31/4155; A61K 31/4184; A61K 31/435; A61K 31/496; A61K 31/50; A61K 31/506; A61K 31/513; A61K 31/5375; A61K 31/5513; A61K 31/59; A61K 31/7008; A61K 31/702; A61K 31/704; A61K 31/7072; A61K 31/716; A61K 31/722; A61K 31/78; A61K 36/07; A61K 36/19; A61K 36/25; A61K 36/27; A61K 36/32; A61K 36/324; A61K 36/35; A61K 36/355; A61K 36/42; A61K 36/534; A61K 36/537; A61K 36/59; A61K 36/63; A61K 36/738; A61K 36/756; A61K 36/81; A61K 36/815; A61K 36/88; A61K 36/906; A61K 41/17; A61K 47/186; A61K 47/36; A61K 8/0233; A61K 8/342; A61K 8/362; A61K 8/4986; A61K 8/63; A61K 8/65; A61K 8/675; A61K 8/738; A61K 8/817; A61K 8/84; A61K 8/85; A61K 8/925; A61K 8/97; A61K 8/9711; A61K 9/0002; A61K 9/0056; A61K 9/10; A61K 9/113; A61K 9/143; A61K 9/146; A61K 9/1611; A61K 9/1641; A61K 9/1652; A61K 9/1658; A61K 9/2077; A61K 9/5031; A61K 9/5052; A61K 9/5073; A61K 9/5094; A61K 9/5138; A61K 9/7053; A61K 2035/115; A61K 2039/542; A61K 2039/552; A61K 2039/55511; A61K 2039/55577; A61K 2039/55583; A61K 2039/55588; A61K 2800/222; A61K 2800/28; A61K 2800/58; A61K 2800/59; A61K 2800/86; A61K 2800/884; A61K 2800/95; A61K 31/045; A61K 31/138; A61K 31/201; A61K 31/203; A61K 31/216; A61K 31/30; A61K 31/365; A61K 31/37; A61K 31/407; A61K 31/415; A61K 31/4178; A61K 31/4188; A61K 31/4192; A61K 31/427; A61K 31/4418; A61K 31/4535; A61K 31/505; A61K 31/536; A61K 31/551; A61K 31/553; A61K 31/566; A61K 31/567; A61K 31/575; A61K 31/592; A61K 31/635; A61K 31/66; A61K 31/7012; A61K 31/7016; A61K 31/7068; A61K 31/714; A61K 31/715; A61K 33/02; A61K 33/22; A61K 33/26; A61K 33/38; A61K 35/20; A61K 35/35; A61K 35/407; A61K 35/60; A61K 35/741; A61K 35/742; A61K 35/745;

A61K 36/14; A61K 36/49; A61K 36/75; A61K 36/84; A61K 36/9062; A61K 38/018; A61K 38/063; A61K 38/1808; A61K 38/19; A61K 38/20; A61K 38/39; A61K 39/12; A61K 39/39; A61K 41/0038; A61K 47/12; A61K 47/14; A61K 47/42; A61K 47/542; A61K 47/545; A61K 47/642; A61K 49/0026; A61K 49/0008; A61K 49/0032; A61K 8/0204; A61K 8/022; A61K 8/042; A61K 8/14; A61K 8/18; A61K 5/28; A61K 8/355; A61K 8/442; A61K 8/463; A61K 8/4946; A61K 8/4953; A61K 8/553; A61K 8/58; A61K 8/606; A61K 8/67; A61K 8/733; A61K 8/8105; A61K 8/892; A61K 8/893; A61K 8/965; A61K 8/9739; A61K 8/9783; A61K 8/981; A61K 9/2027; A61K 9/2059; A61K 9/7038; A61P 19/06; A61P 17/00; A61P 17/10; A61P 43/00; A61P 35/00; A61P 29/00; A61P 5/30; A61P 25/28; A61P 15/12; A61P 17/02; A61P 17/16; A61P 15/00; A61P 13/08; A61P 9/00; A61P 25/24; A61P 3/06; A61P 9/12; A61P 19/10; A61P 25/00; A61P 17/14; A61P 25/20; A61P 25/22; A61P 3/00; A61P 5/24; A61P 1/00; A61P 17/18; A61P 9/10; A61P 39/06; A61P 3/04; A61P 17/04; A61P 7/04; A61P 17/08; A61P 19/02; A61P 5/32; A61P 17/06; A61P 3/10; A61P 5/26; A61P 15/08; A61P 1/04; A61P 25/04; A61P 35/02; A61P 5/28; A61P 15/02; A61P 15/10; A61P 17/12; A61P 27/12; A61P 3/02; A61P 39/00; A61P 5/14; A61P 5/50; A61P 23/02; A61P 35/04; A61P 5/16; A61P 25/06; A61P 25/16; A61P 27/02; A61P 15/14; A61P 37/00; A61P 5/00; A61P 19/00; A61P 21/00; A61P 25/02; A61P 19/04; A61P 25/14; A61P 1/02; A61P 13/02; A61P 25/30; A61P 29/02; A61P 31/04; A61P 7/00; A61P 7/10; A61P 1/16; A61P 37/06; A61P 37/08; A61P 1/12; A61P 11/00; A61P 11/14; A61P 13/00; A61P 27/06; A61P 9/04; A61P 21/06; A61P 25/08; A61P 27/16; A61P 3/14; A61P 41/00; A61P 9/14; A61P 1/08; A61P 11/06; A61P 11/08; A61P 13/12; A61P 19/08; A61P 21/04; A61P 25/18; A61P 31/12; A61P 31/14; A61P 31/18; A61P 37/02; A61P 7/12; A61Q 19/08; A61Q 19/00; A61Q 19/02; A61Q 17/04; A61Q 19/007; A61Q 19/10; A61Q 7/00; A61Q 19/04; A61Q 5/02; A61Q 19/06; A61Q 19/008; A61Q 5/12; A61Q 19/004; A61Q 17/00; A61Q 3/00; A61Q 5/00; A61Q 5/06; A61Q 9/02; A61Q 1/02; A61Q 5/10; A61Q 11/00; A61Q 19/005; A61Q 9/04; A61Q 3/02; A61Q 5/065; A61Q 1/10; A61Q 1/12; A61Q 13/00; A61Q 15/00; A61Q 17/005; A61Q 5/002; A61Q 5/04; A61Q 7/02; A61Q 1/00; A61Q 1/14

See application file for complete search history.

(56) References Cited

FOREIGN PATENT DOCUMENTS

| | | |
|---|---|---|
| CN | 111388461 A | 7/2020 |
| CN | 113440516 A | 9/2021 |
| WO | 2006024545 A1 | 3/2006 |
| WO | 111166740 A | 5/2020 |
| WO | 2021158573 A1 | 8/2021 |

OTHER PUBLICATIONS

J Ma et al. "Inhibitory Effect of Pueraria Isoflavones on α-Glucosidase and Structure-Effect Analysis" Chinese Traditional Patent Medicine, vol. 37, No. 4, pp. 858-862 (Apr. 20, 2015).

Hang Su et al., "In vitro and in vivo inhibitory activity of taxifolin on three digestive enzymes" International Journal of Biological Macromolecules 150 (2020) 31-37 (Feb. 5, 2020).

Chao Li et al., "pH-promoted alpha-glucosylation of flavonoids using an engineered alpha-glucosidase mutant" Bioorganic Chemistry 107 (2021) 104581 (Dec. 28, 2020).

Vipin Kumar et al., "Pharmacophore modeling and 3D-QSAR studies on flavonoids as alpha-glucosidase inhibitors" Der Pharma Chemica, 2010, 2(4): 324-335 (Dec. 31, 2010).

* cited by examiner

COMPOSITION FOR INHIBITING ALPHA-GLUCOSIDASE AND APPLICATION THEREOF

This application is a Continuation Application of PCT/CN2022/111359, filed on Aug. 10, 2022, which claims priority to Chinese Patent Application No. 202110962157.2, filed on Aug. 20, 2021, which is incorporated by reference for all purposes as if fully set forth herein.

TECHNICAL FIELD

The present invention belongs to the technical field of natural active compounds, and in particular relates to a composition for inhibiting α-glucosidase and application thereof.

BACKGROUND

The progress of the times has led to rapid development of science and technology, people's living standards have been also continuously improved due to the progress of science, and people's eating habits have also undergone great changes. Unscientific large ingestion such as high glucose, high protein and high fat, results in a significant increase in the incidence of some "rich mans disease", and diabetes mellitus is one of them. Diabetes mellitus is a global chronic metabolic disease that remains a lifelong disease that cannot be completely cured. The main feature of the disease is that glucose concentration in the blood is at a high level for a long time and glucose can be detected in urine. It is an important means to inhibit the increase of postprandial blood glucose by controlling activity of α-glucosidase.

Daidzein is a natural isoflavone compound of plant estrogen. The daidzein mainly has pharmacological effects on anti-cancer, anti-thrombosis, anti-cardiovascular diseases, hypoglycemic and other physiological activities. Therefore, the daidzein is often widely used as a pharmaceutical drug and food supplement. Dietary soy isoflavone has been shown to have a relief effect on type II diabetes. Cho and other studies found that the daidzein increases the expression of GLUT4 and IRS-1 by activating PPARγ, thereby improving the uptake of glucose by insulin-stimulated adipocytes. These studies further support recent research results, where the beneficial effects of dietary soy isoflavone on diabetes may be attributed to daidzein and the daidzein metabolite, equol (Cho, K. W., Lee, O. H., Banz, W. J., Moustaid-Moussa, N., Shay, N. F., Kim, Y. C., 2010. Daidzein and the daidzein metabolite, equol, enhance adipocyte differentiation and PPARγ transcriptional activity. J Nutr Biochem 21, 841-847).

The ultimate purpose of combination of active molecules is to improve the effect, reduce the dosage, reduce the toxic side effects, and avoid or delay the development of resistance. Therefore, it is of great significance to study the combination of flavonoid compounds to inhibit the α-glucosidase and improve hypoglycemic activity for improving human health.

SUMMARY

The purpose of the present invention is to provide a composition for inhibiting α-glucosidase and application thereof, so as to solve a problem in the prior art that a single active component has a limited hypoglycemic effect and is prone to generate drug resistance.

In order to achieve the above purpose, the present invention is implemented by the following technical solutions:

a composition, containing daidzein and quercetin derivatives; where the quercetin derivative is taxifolin or 3-O-methyl quercetin, where the mass ratio of the daidzein to the taxifolin is 8:25-10:25; and the mass ratio of the daidzein to the 3-O-methyl quercetin is 8:2-8:4.

In several specific embodiments, the mass ratio of the daidzein to the taxifolin is 8:25, 10:25, where when the mass ratio of the daidzein to the taxifolin is 8:25, an average (CIavg) of combination thereof is 0.82, which is better than that at the mass ratio of 10:25, and has a relatively strong synergistic effect.

In several specific embodiments, the mass ratio of the daidzein to the 3-O-methyl quercetin is 8:2, 8:4, where when the mass ratio of the daidzein to the 3-O-methylquercetin is 8:2, an average (CIavg) of combination index thereof is 0.6, which is better than that at the mass ratio of 8:4, and has a relatively strong synergistic effect.

Application of the above composition in the preparation of a formulation having an effect of inhibiting α-glucosidase.

An α-glucosidase inhibitor, an effective component thereof contains daidzein and taxifolin, or daidzein and 3-O-methyl quercetin, where the mass ratio of the daidzein to the taxifolin is 8:25-10:25; and the mass ratio of the daidzein to the 3-O-methyl quercetin is 8:2-8:4.

Application of the above composition in the preparation of a drug having a hypoglycemic effect, where the hypoglycemic effect is to block digestion and absorption of carbohydrates by inhibiting activity of α-glucosidase to achieve a purpose of controlling postprandial hyperglycemia.

A medicine having a hypoglycemic effect, effective components thereof contain daidzein and taxifolin, or daidzein and 3-O-methyl quercetin, where the mass ratio of the daidzein to the taxifolin is 8:25-10:25; and the mass ratio of the daidzein to the 3-O-methyl quercetin is 8:2-8:4.

Within the limited mass ratio, daidzein and taxifolin, daidzein and 3-O-methyl quercetin achieve synergistic technical effects.

The drug in the present invention contains a carrier, a solvent, a diluent, and an excipient acceptable in pharmacy that are mixed with other mediums, and may be prepared into powder, granules, capsules, injection, oral liquid, or tablets according to different demands.

Advantages of the technical solutions of the present invention:

The composition of daidzein and taxifolin, daidzein and 3-O-methyl quercetin of the present invention has a significant synergistic effect of inhibiting α-glucosidase, the effect of the composition is superior to that of using the flavonoids alone, and can reduce the dosage used by drugs and reduce the occurrence of drug resistance. Through an in vitro α-glucosidase inhibition test, using a Chou-Talalay method, it is proved that the composition of daidzein and taxifolin, daidzein and 3-O-methyl quercetin of the present invention has a significant synergistic effect on α-glucosidase at mass ratio of 8:25 and 8:2 respectively. The CI values at 50% (GI50), 75% (GI75) and 90% (GI90) inhibition rates are all less than 1.0, and the strength of synergistic effect between drugs at high inhibition rates is generally higher than that at low inhibition rates.

DETAILED DESCRIPTION OF THE EMBODIMENTS

Figure 1:
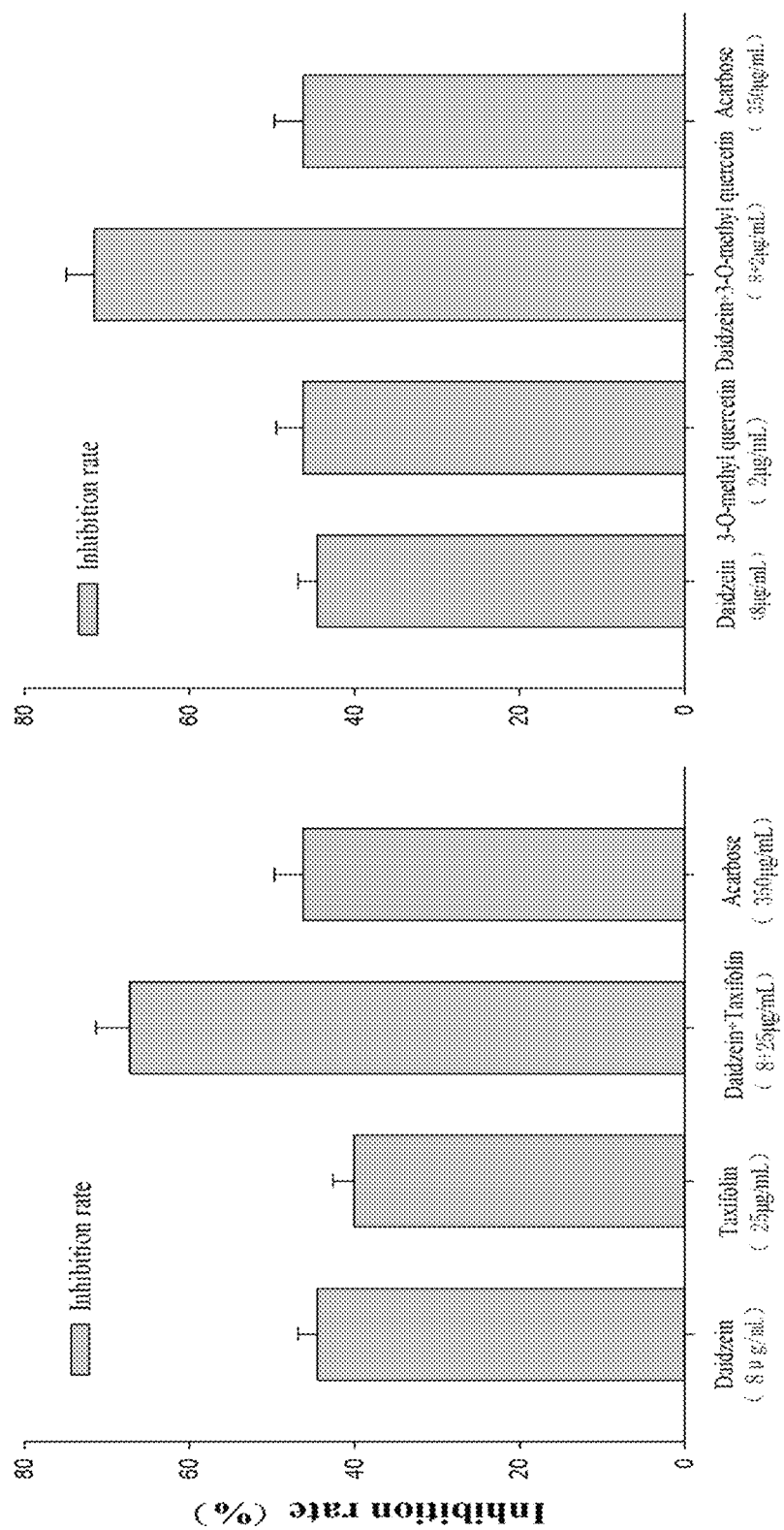
FIG. 1 is an inhibitory activity of daidzein compositions of Example 1 and Example 5 on α-glucosidase.

The terms used in the present invention, unless otherwise specified, generally have meanings normally understood by those of ordinary skills in the art.

Daidzein, molecular formula is C15H10O4; molecular weight is: 254.24; and CAS accession number is: 486-66-8, and structural formula is:

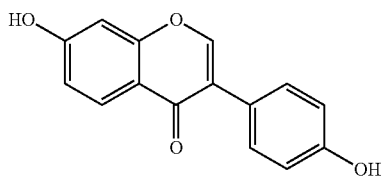 [SMILES: O=c1c(-c2ccc(O)cc2)coc2cc(O)ccc12]

Taxifolin, molecular formula is C15H12O7; molecular weight is: 304.25; and CAS accession number is: 480-18-2, and structural formula is:

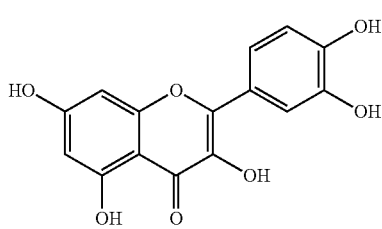 [SMILES: O=c1c(O)c(-c2ccc(O)c(O)c2)oc2cc(O)cc(O)c12]

3-O-Methyl Quercetin, molecular formula is C16H12O7; molecular weight is: 316.26; and CAS accession number is: 1486-70-0, and structural formula is:

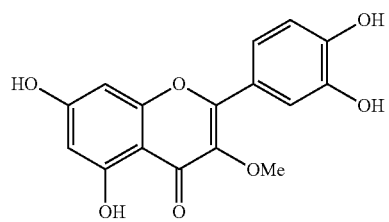 [SMILES: COc1c(-c2ccc(O)c(O)c2)oc2cc(O)cc(O)c2c1=O]

α-glucosidase (coming from *Saccharomyces cerevisiae*, Sigma);

4-nitrophenyl-α-D-glucopyranoside (pNPG, TOKYO Chemica Industry Co., LTD);

acarbose (Acarbose, TOKYO Chemica Industry Co., LTD);

daidzein, taxifolin, and 3-O-methyl quercetin (Solarbio, Beijing);

Millipore Simplicity water purification system (Millipore, France);

sodium phosphate salt buffer solution (pH 6.8, 0.1 mol L−1); and enzyme-linked analyzer TECAN infinite M200 PRO (Teacan Group Ltd., Switzerland).

The present invention will be described in further detail in conjunction with specific embodiments and with reference to data. The following examples are intended only to illustrate the present invention and are not intended to limit the scope of the present invention in any way.

Example 1

A composition of daidzein and taxifolin, where the mass ratio of the daidzein to the taxifolin is 8:25, and specific concentrations of daidzein and taxifolin in the composition are 8 μg/mL and 25 μg/mL respectively.

Example 2

A composition of daidzein and taxifolin, where the mass ratio of the daidzein to the taxifolin is 8:30, and specific concentrations of daidzein and taxifolin in the composition are 8 μg/mL and 30 μg/mL respectively.

Example 3

A composition of daidzein and taxifolin, where the mass ratio of the daidzein to the taxifolin is 8:50, and specific concentrations of daidzein and taxifolin in the composition are 8 μg/mL and 50 μg/mL respectively.

Example 4

A composition of daidzein and taxifolin, where the mass ratio of the daidzein to the taxifolin is 10:25, and specific concentrations of daidzein and taxifolin in the composition are 10 μg/mL and 25 μg/mL respectively.

Example 5

A composition of daidzein and 3-O-methyl quercetin, where the mass ratio of the daidzein to the 3-O-methyl quercetin is 8:2, and specific concentrations of daidzein and 3 methyl quercetin in the composition are 8 μg/mL and 2 μg/mL respectively.

Example 6

A composition of daidzein and 3-O-methyl quercetin, where the mass ratio of the daidzein to the 3-O-methyl quercetin is 8:4, and specific concentrations of daidzein and 3-O-methyl quercetin in the composition are 8 μg/mL and 4 μg/mL respectively.

Example 7

A composition of daidzein and 3-O-methyl quercetin, where the mass ratio of the daidzein to the 3-O-methyl quercetin is 8:6, and specific concentrations of daidzein and 3-O-methyl quercetin in the composition are 8 μg/mL and 6 μg/mL respectively.

Example 8

A composition of daidzein and 3-O-methyl quercetin, where the mass ratio of the daidzein to the 3-O-methyl quercetin is 10:2, and specific concentrations of daidzein and 3-O-methyl quercetin in the composition are 10 μg/mL and 2 μg/mL respectively.

Test for Hypoglycemic Effect of Daidzein Composition

Experimental Method:

an α-glucosidase solution with a concentration being 0.25 U/mL and a substrate p-nitrophenyl-α-D-glucopyranoside (pNPG) solution with a concentration being 5 mmol/mL were prepared by using a PBS buffer solution (0.1 mol L−1 pH 6.8).

40 μL α-glucosidase solution was accurately removed, 100 μL of sample solution to be tested was added respectively, reacted for 10 min at 37° C., then 60 μL of substrate p-nitrophenyl-α-D-glucopyranoside (pNPG) solution was added, reacted for 15 min at 37° C., and an enzyme-linked analyzer measured at a wavelength of 405 nm.

The solution of the sample to be tested is the daidzein composition of Examples 1-8. First, daidzein, taxifolin, and 3-O-methyl quercetin were respectively prepared into 10 mg/mL mother solutions by using dimethyl sulfoxide (DMSO); and then a sample solution of the specific concentration of the daidzein, taxifolin, and 3-O-methyl quercetin and composition was prepared with PBS buffer solution.

A positive control group was acarbose (350 μg/mL), a blank group was that samples and enzymes were not added, and a sample blank group was that enzymes were not added.

inhibition rate=[1−(ODsample−ODsample blank)/(ODnegative control−ODblank)]×100%   Calculation formula CI values are calculated according to CompuSyn software to evaluate synergistic effect among drugs.

Combination Index (CI) is used to describe the strength of the synergistic effect of the drugs; CI<1 represents that the synergistic effect exists among drugs, combination can strengthen the therapeutic effect of various monomer drugs, and the smaller the CI values, the stronger the synergistic effect; CI=1 represents that adduction exists among drugs, and a combination result is just linear superposition of the therapeutic effect of various monomer drugs; and CI>1 represents that an antagonistic effect exists among drugs, and combination may reduce the therapeutic effect of each monomer drug inversely.

1. Inhibitory Activity of Daidzein Compositions of Example 1 and Example 5 on α-Glucosidase The inhibitory activity of daidzein compositions of Example 1 and Example 5 on α-glucosidase is as shown in FIG. 1: inhibition rates of 8 μg/mL daidzein, 25 μg/mL taxifolin, 2 μg/mL 3-O-methyl quercetin and 350 μg/mL acarbose at the corresponding mass concentrations on α-glucosidase are 44.5±2.5%, 40.12±2.1%, 46.23±1.2%, 46.25±3.5% respectively; the inhibition rates of the daidzein and taxifolin composition (8+25 μg/mL) is 67.25±3.35%, and the inhibition rates of the daidzein and 3-O-methyl quercetin (8+2 μg/mL) is 71.56±3.4%. The results show that the composition greatly improves the inhibitory activity on α-glucosidase when used in combination.

Figure 2:
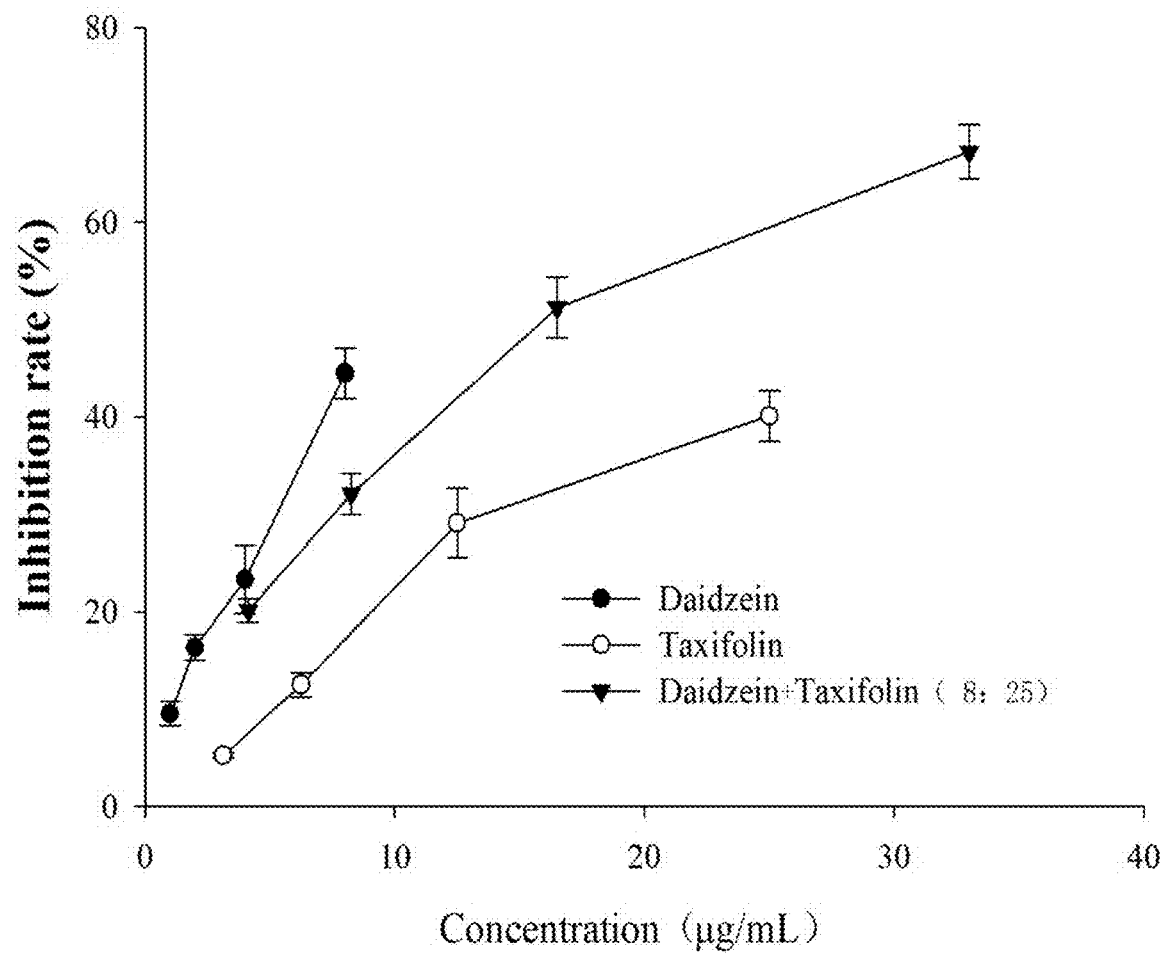
FIG. 2 is an inhibition curve graph of α-glucosidase by a daidzein+taxifolin (8:25) composition.
Figure 3:
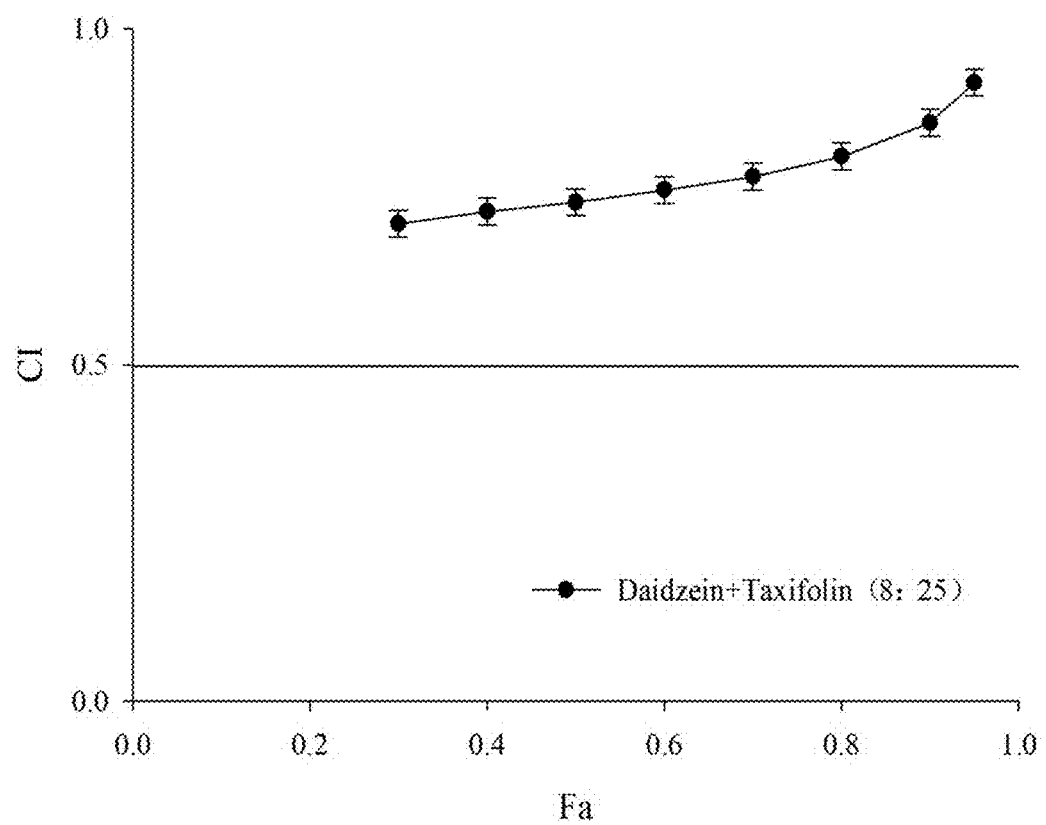
FIG. 3 is a Fa-CI trend graph of α-glucosidase by a daidzein+taxifolin (8:25) composition.

The α-glucosidase inhibitory activity of the daidzein and taxifolin composition at a mass ratio of 8:25 is tested at different concentration gradients, and the concentration gradient of the daidzein and taxifolin composition is (μg/mL): 8+25, 4+12.5, 2+6.25, 1+3.125; the concentration gradient of the daidzein is (μg/mL): 8, 4, 2, 1; and the concentration gradient of the taxifolin is (μg/mL): 25, 12.5, 6.25, 3.125. The results are as shown in FIG. 2: a daidzein and taxifolin composition at a mass ratio of 8:25 increased the inhibitory activity on α-glucosidase at different concentration gradients. The Fa-CI trend graph of a daidzein and taxifolin composition with a mass ratio of 8:25 is as shown in FIG. 3, and it can be seen from FIG. 3 that the CI values of daidzein and taxifolin are both below 1.0, showing a synergistic effect.

Figure 4:
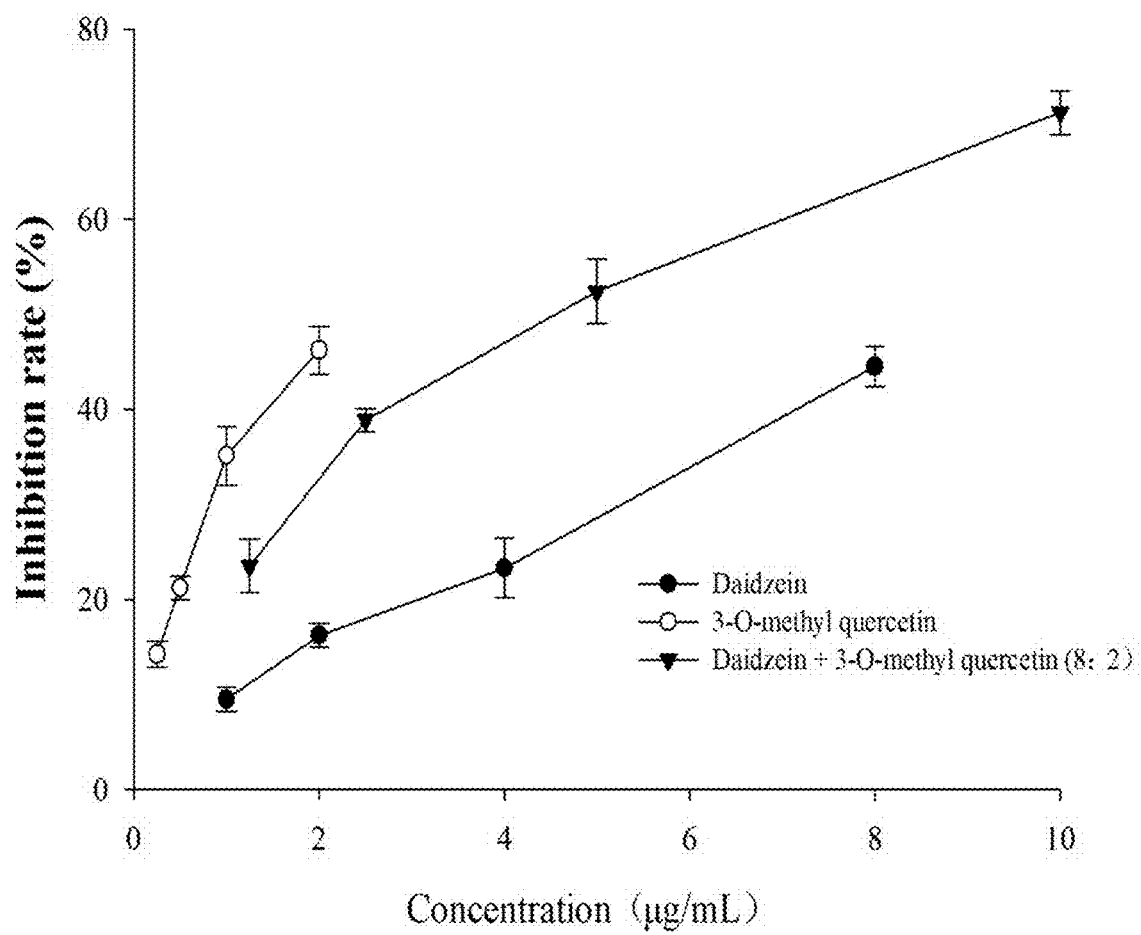
FIG. 4 is an inhibition curve graph of α-glucosidase by a daidzein+3-O-methyl quercetin (8:2) composition.
Figure 5:
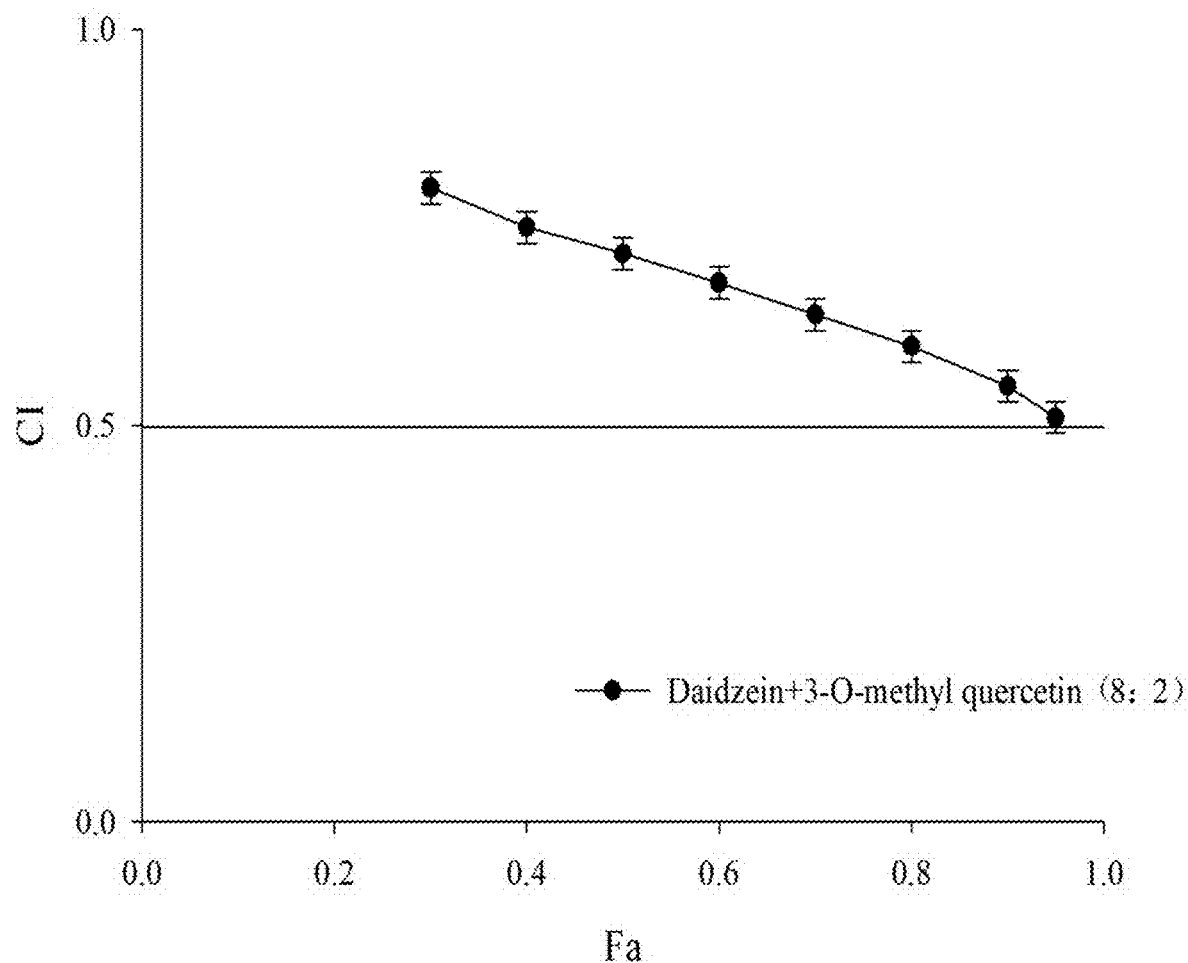
FIG. 5 is a Fa-CI trend graph for inhibition of α-glucosidase by a daidzein+3-O-methyl quercetin (8:2) composition.

The α-glucosidase inhibitory activity of the daidzein and 3-O-methyl quercetin composition at a mass ratio of 8:2 is tested at different concentration gradients, and the concentration gradient of the daidzein and 3-O-methyl quercetin composition was (μg/mL): 8+2, 4+1, 2+0.5, 1+0.25; the concentration gradient of the daidzein was (μg/mL): 8, 4, 2, 1; and the concentration gradient of the 3-O-methyl quercetin was (μg/mL): 2, 1, 0.5, 0.25. The results are shown in FIG. 4: a daidzein and 3-O-methyl quercetin composition at a mass ratio of 8:2 also correspondingly increased the inhibitory activity on α-glucosidase at different concentration gradients. The Fa-CI trend graph of a daidzein and 3-O-methyl quercetin composition at a mass ratio of 8:2 is as shown in FIG. 5, and it can be seen from FIG. 5 that the CI values of daidzein and 3-O-methyl quercetin are both below 1.0, showing a synergistic effect. The combination index (CI) of the daidzein composition of Example 1 and Example 5 is shown in Table 1:

TABLE 1

| | Combination index (CI) of the daidzein composition of Example 1 and Example 5 | | | | |
|---|---|---|---|---|---|
| | Mass | CI | | | |
| Compound | ratio | GI$_{50}$ | GI$_{75}$ | GI$_{90}$ | CI$_{avg}$ |
| Daidzein + taxifolin | 8:25 | 0.74 ± 0.01 | 0.79 ± 0.02 | 0.86 ± 0.01 | 0.82 |
| Daidzein + 3-O-methyl quercetin | 8:2 | 0.71 ± 0.02 | 0.62 ± 0.03 | 0.55 ± 0.02 | 0.60 |

Data comes from results of three independent experiments and is represented as average value±standard difference From the results in Table 1, it can be seen that when a combination of the daidzein and taxifolin (8:25) and a combination of the daidzein and 3-O-methyl quercetin (8:2) are used, the combination indexes (CI) both are less than 1, showing a synergistic effect, where an average of combination index (CI$_{avg}$) of the daidzein and taxifolin (8:25) is 0.82, showing a synergistic effect; and an average of combination index ($CI_{avg}$) of the daidzein and 3-O-methyl quercetin (8:2) is 0.60, showing a relatively strong synergistic effect.

Figure 6:
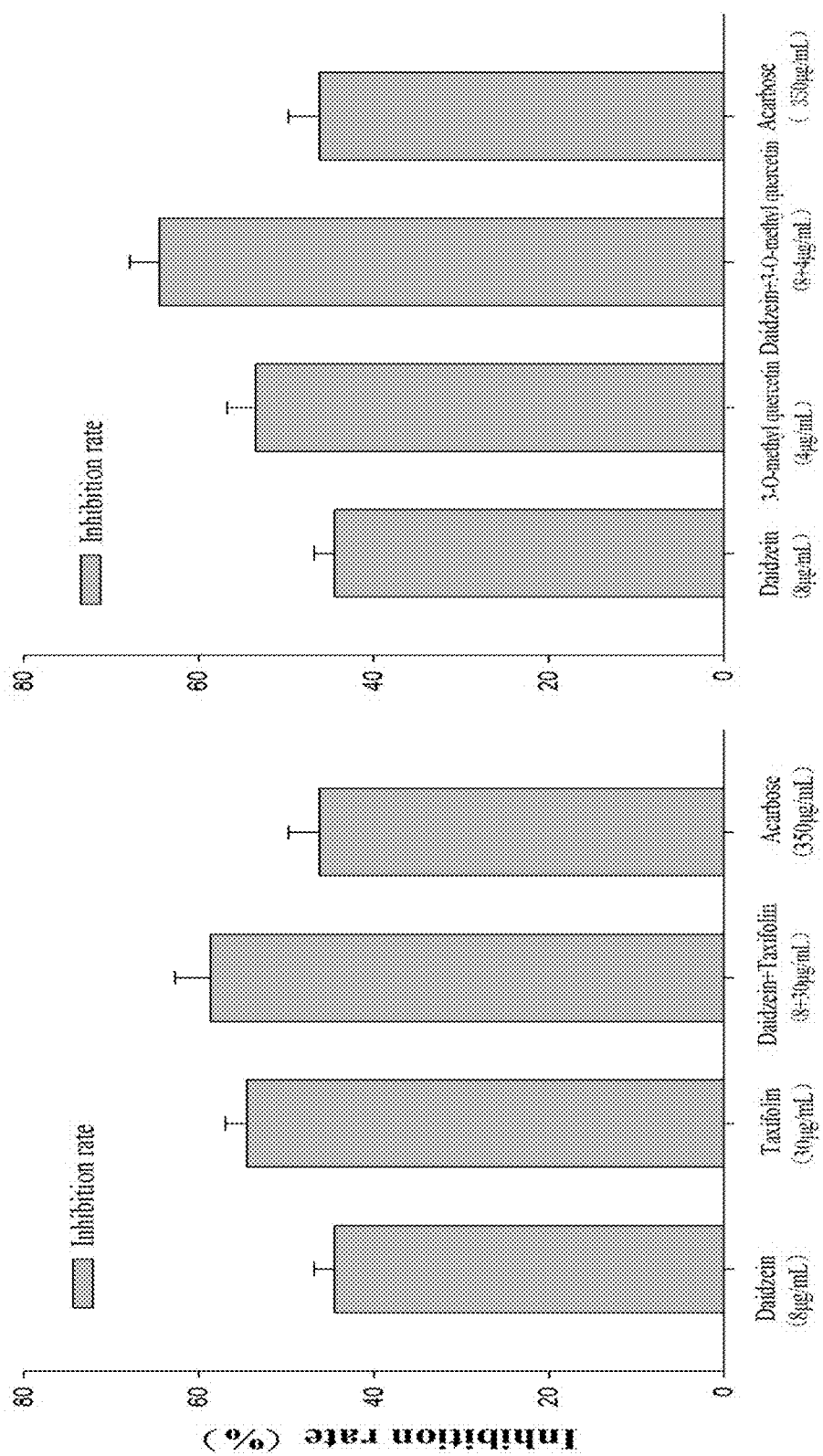
FIG. 6 is an inhibitory activity of daidzein compositions of Example 2 and Example 6 on α-glucosidase.

2. Inhibitory Activity of Daidzein Compositions of Example 2 and Example 6 on α-Glucosidase The inhibitory activity of daidzein compositions of Example 2 and Example 6 on α-glucosidase is shown in FIG. 6: inhibition rates of 8 μg/mL daidzein, 30 μg/mL taxifolin, 4 μg/mL 3-O-methyl quercetin and 350 μg/mL acarbose at the corresponding mass concentrations on α-glucosidase are 44.5±2.5%, 54.5±2.4%, 53.52±3.2%, 46.25±3.5% respectively; the inhibition rates of the daidzein and taxifolin composition (8+30 μg/mL) is 58.6±3.5%, and the inhibition rates of the daidzein and 3-O-methyl quercetin (8+4 μg/mL) is 64.5±2.4%. The results show that the composition improves the inhibitory activity of α-glucosidase when used in combination.

Figure 7:
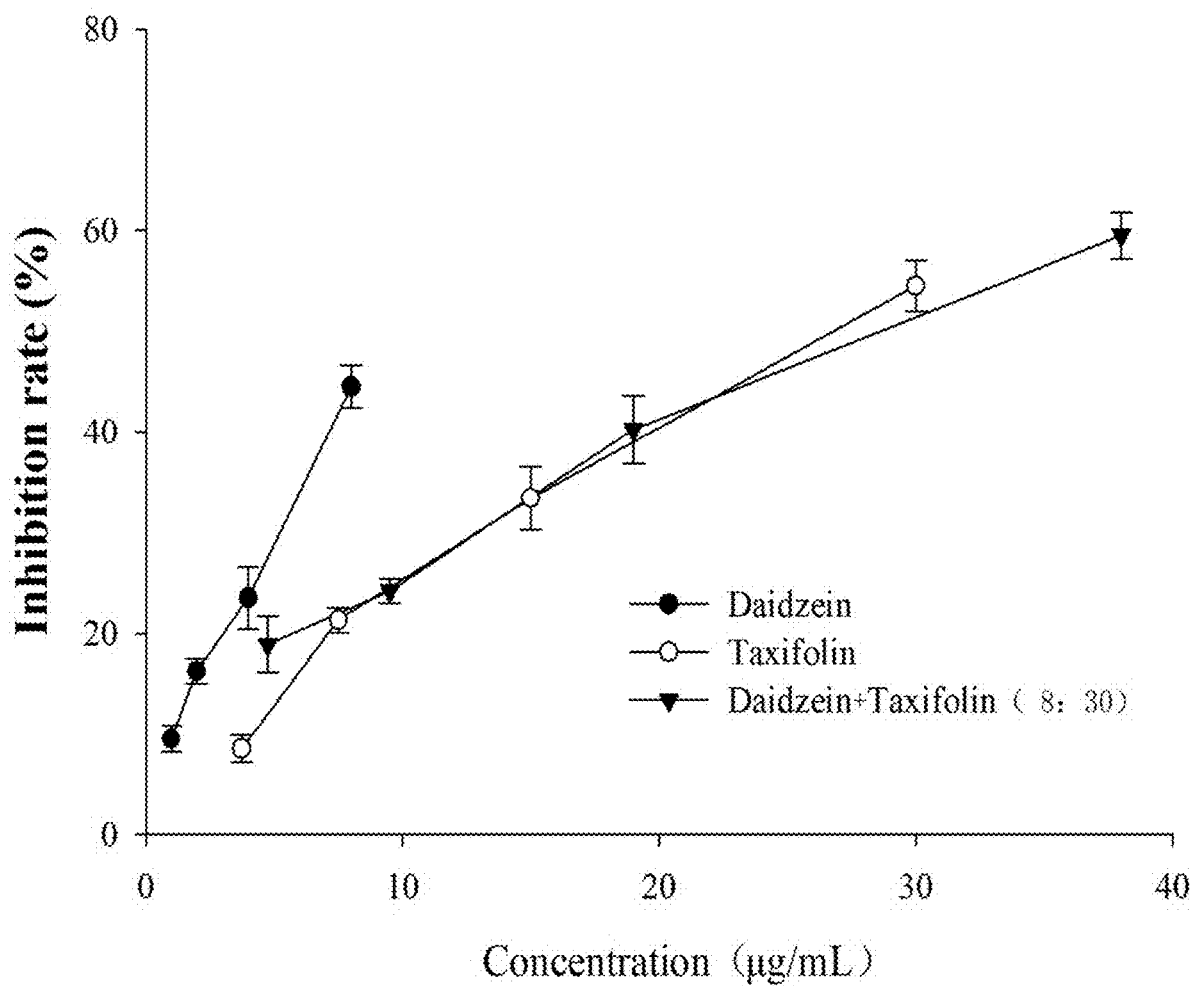
FIG. 7 is an inhibition curve graph of α-glucosidase by a daidzein+taxifolin (8:30) composition.

The α-glucosidase inhibitory activity of the daidzein and taxifolin composition at a mass ratio of 8:30 is tested at different concentration gradients, and the concentration gradient of the daidzein and taxifolin composition is (μg/mL): 8+30, 4+15, 2+7.5, 1+3.75; the concentration gradient of the daidzein is (μg/mL): 8, 4, 2, 1; the concentration gradient of the taxifolin is (μg/mL): 30, 15, 7.5, 3.75; and the results are shown in FIG. 7.

Figure 8:
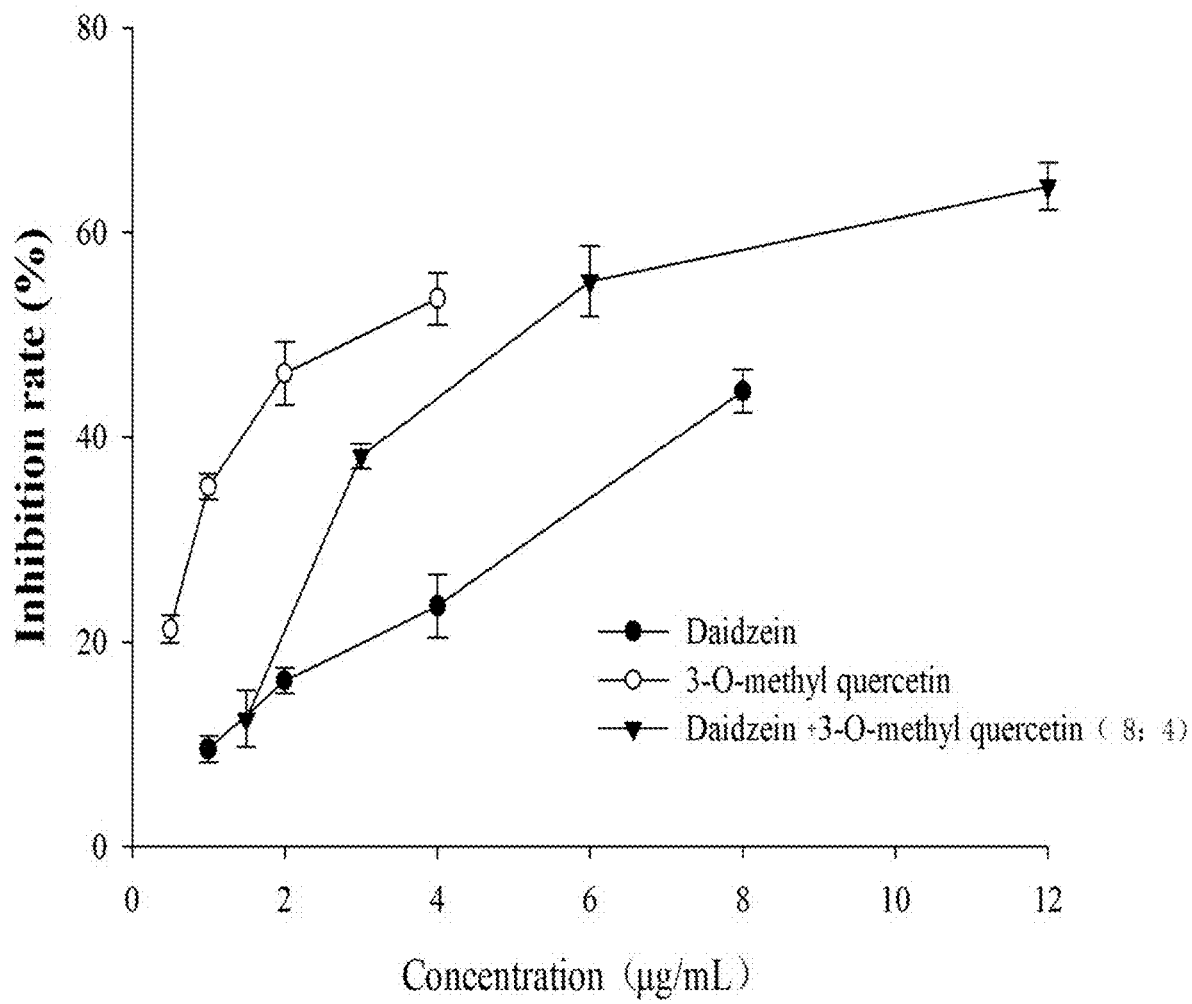
FIG. 8 is an inhibition curve graph of α-glucosidase by a daidzein+3-O-methyl quercetin (8:4) composition.

The α-glucosidase inhibitory activity of the daidzein and 3-O-methyl quercetin composition at a mass ratio of 8:4 is tested at different concentration gradients, and the concentration gradient of the daidzein and 3-O-methyl quercetin composition is (μg/mL): 8+4, 4+2, 2+1, 1+0.5; the concentration gradient of the daidzein is (μg/mL): 8, 4, 2, 1; the concentration gradient of the 3-O-methyl quercetin is (μg/mL): 4, 2, 1, 0.5; and the results are shown in FIG. 8. The combination index (CI) of the daidzein composition of Example 2 and Example 6 is shown in Table 2:

TABLE 2

Combination index (CI) of the daidzein composition of Example 2 and Example 6

| Compound | Mass ratio | CI | | | |
| --- | --- | --- | --- | --- | --- |
| | | $GI_{50}$ | $GI_{75}$ | $GI_{90}$ | $CI_{avg}$ |
| Daidzein + taxifolin | 8:30 | >1 | >1 | >1 | >1 |
| Daidzein + 3-O-methyl quercetin | 8:4 | 1.09 ± 0.02 | 0.96 ± 0.02 | 0.84 ± 0.02 | 0.92 |

Data comes from results of three independent experiments and is represented as average value±standard difference From the results in Table 2, it can be seen that although a combination of the daidzein and taxifolin (8:30) composition and a combination of the daidzein and 3-O-methyl quercetin (8:4) have improved inhibitory activity on α-glucosidase; however, when the combination of the daidzein and taxifolin (8:30) composition is used, the combination index (CI) is greater than 1, showing an antagonistic effect; and when the combination of the daidzein and 3-O-methyl quercetin (8:4) is used, the combination index (CI) is close to 1, showing a weak synergistic effect.

Figure 9:
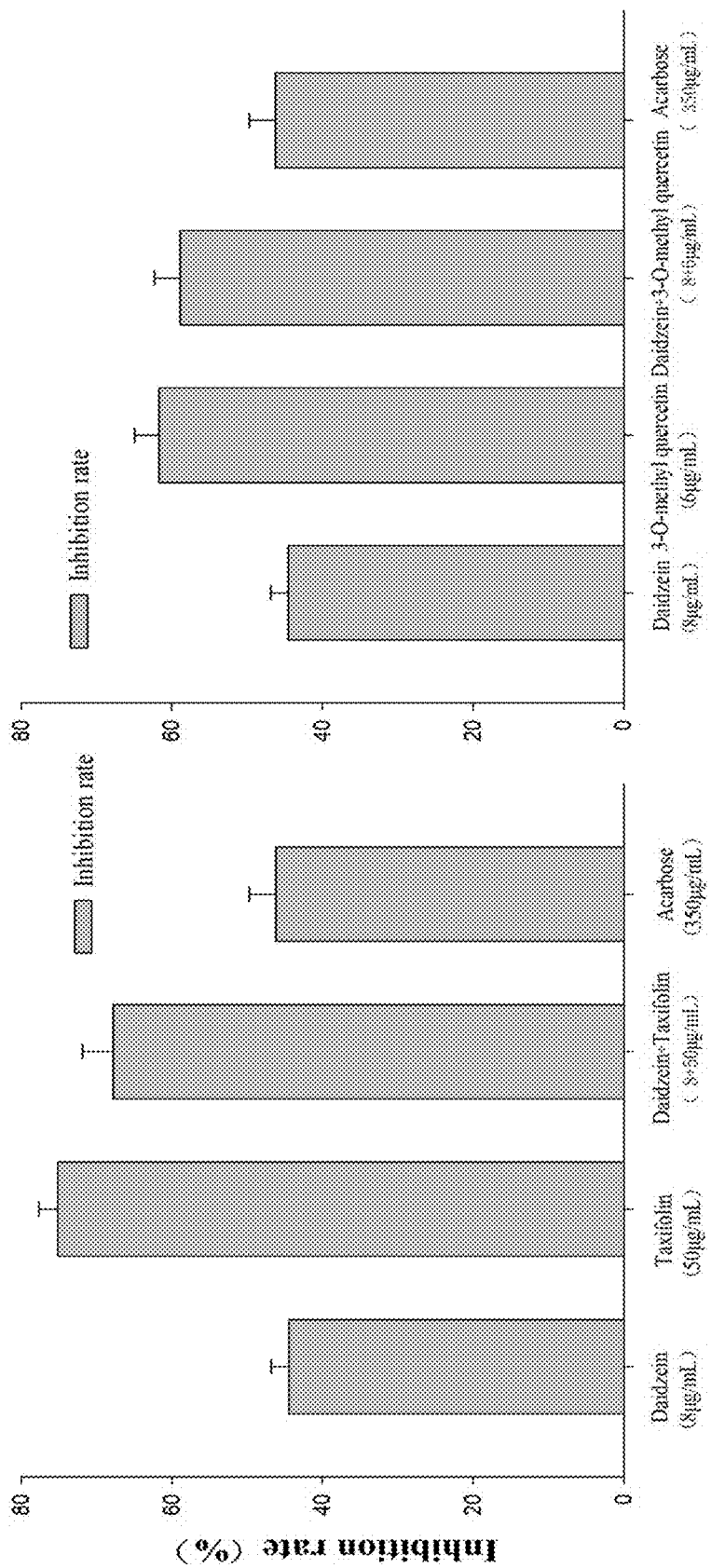
FIG. 9 is an inhibitory activity of daidzein compositions of Example 3 and Example 7 on α-glucosidase.

3. Inhibitory Activity of Daidzein Compositions of Example 3 and Example 7 on α-Glucosidase The inhibitory activity of daidzein compositions of Example 3 and Example 7 on α-glucosidase is shown in FIG. 9: inhibition rates of 8 μg/mL daidzein, 50 μg/mL taxifolin, 6 μg/mL 3-O-methyl quercetin and 350 μg/mL acarbose at the corresponding mass concentrations on α-glucosidase are 44.5±2.5%, 75.21±3.4%, 61.72±3.5%, 46.25±3.5% respectively; the inhibition rates of the daidzein and taxifolin composition (8+50 μg/mL) is 67.8±3.7%, and the inhibition rates of the daidzein and 3-O-methyl quercetin (8+6 μg/mL) is 58.9±3.4%. The results show that the composition does not significantly improve the inhibitory activity on α-glucosidase when used in combination.

Figure 10:
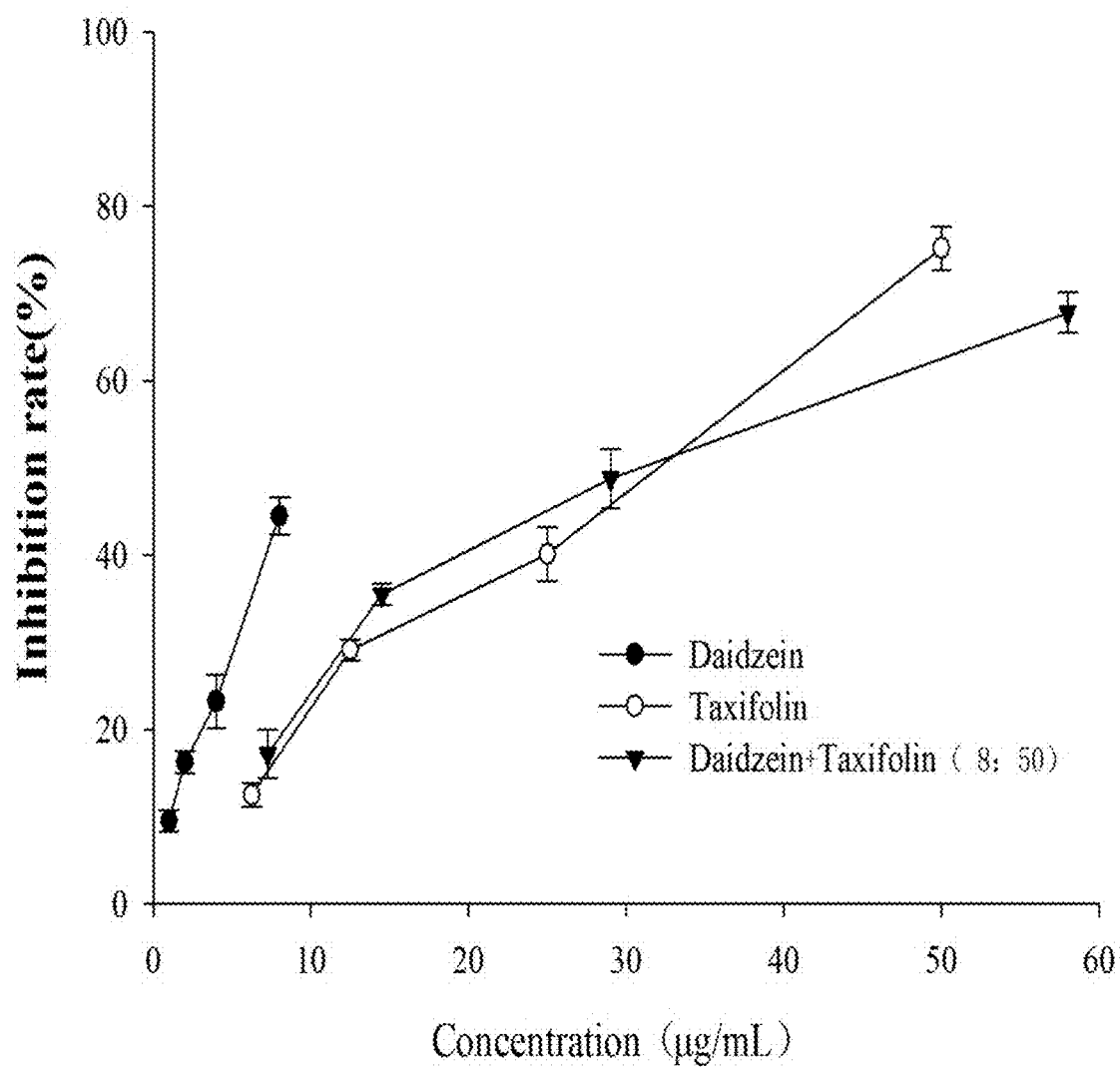
FIG. 10 is an inhibition curve graph of α-glucosidase by a daidzein+taxifolin (8:50) composition.

The α-glucosidase inhibitory activity of the daidzein and taxifolin composition at a mass ratio of 8:50 is tested at different concentration gradients, and the concentration gradient of the daidzein and taxifolin composition is (μg/mL): 8+50, 4+25, 2+12.5, 1+6.25; the concentration gradient of the daidzein is (μg/mL): 8, 4, 2, 1; the concentration gradient of the taxifolin is (μg/mL): 50, 25, 12.5, 6.25; and the results are shown in FIG. 10.

Figure 11:
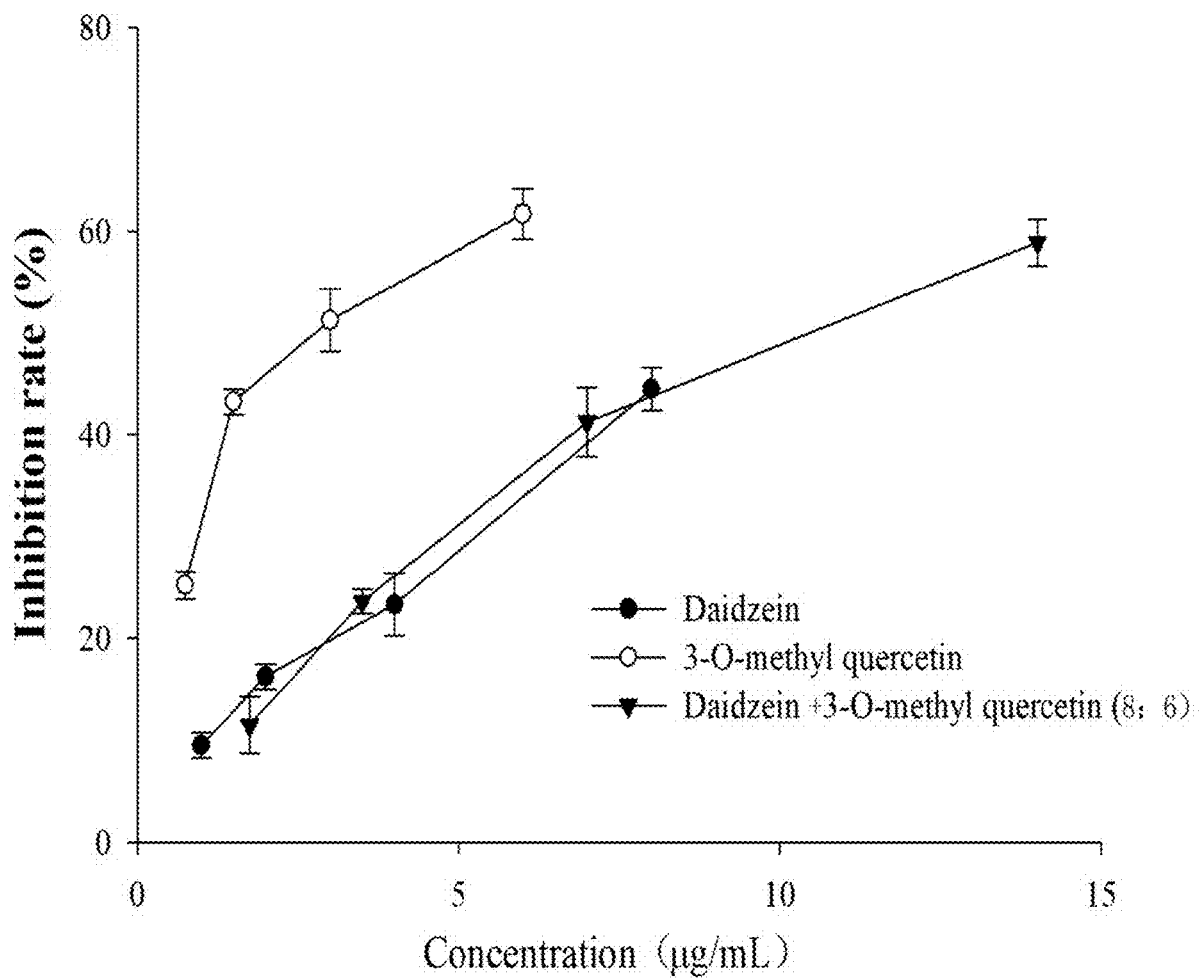
FIG. 11 is an inhibition curve graph of α-glucosidase by a daidzein+3-O-methyl quercetin (8:6) composition.

The α-glucosidase inhibitory activity of the daidzein and 3-O-methyl quercetin composition at a mass ratio of 8:6 is tested at different concentration gradients, and the concentration gradient of the daidzein and 3-O-methyl quercetin composition is (μg/mL): 8+6, 4+3, 2+1.5, 1+0.75; the concentration gradient of the daidzein is (μg/mL): 8, 4, 2, 1; the concentration gradient of the 3-O-methyl quercetin is (μg/mL): 6, 3, 1.5, 0.75; and the results are shown in FIG. 11.

The combination index (CI) of the daidzein composition of Example 3 and Example 7 is shown in Table 3:

TABLE 3

Combination index (CI) of the daidzein composition of Example 3 and Example 7

| Compound | Mass ratio | CI | | | |
| --- | --- | --- | --- | --- | --- |
| | | $GI_{50}$ | $GI_{75}$ | $GI_{90}$ | $CI_{avg}$ |
| Daidzein + taxifolin | 8:50 | >1 | >1 | >1 | >1 |
| Daidzein + 3-O-methyl quercetin | 8:6 | >1 | >1 | >1 | >1 |

Data comes from results of three independent experiments and is represented as average value±standard difference From the results in Table 3, it can be seen that when a combination of the daidzein and taxifolin (8:50) and a combination of the daidzein and 3-O-methyl quercetin (8:6) composition are used, the combination indexes (CI) both are greater than 1, showing an antagonistic effect.

Figure 12:
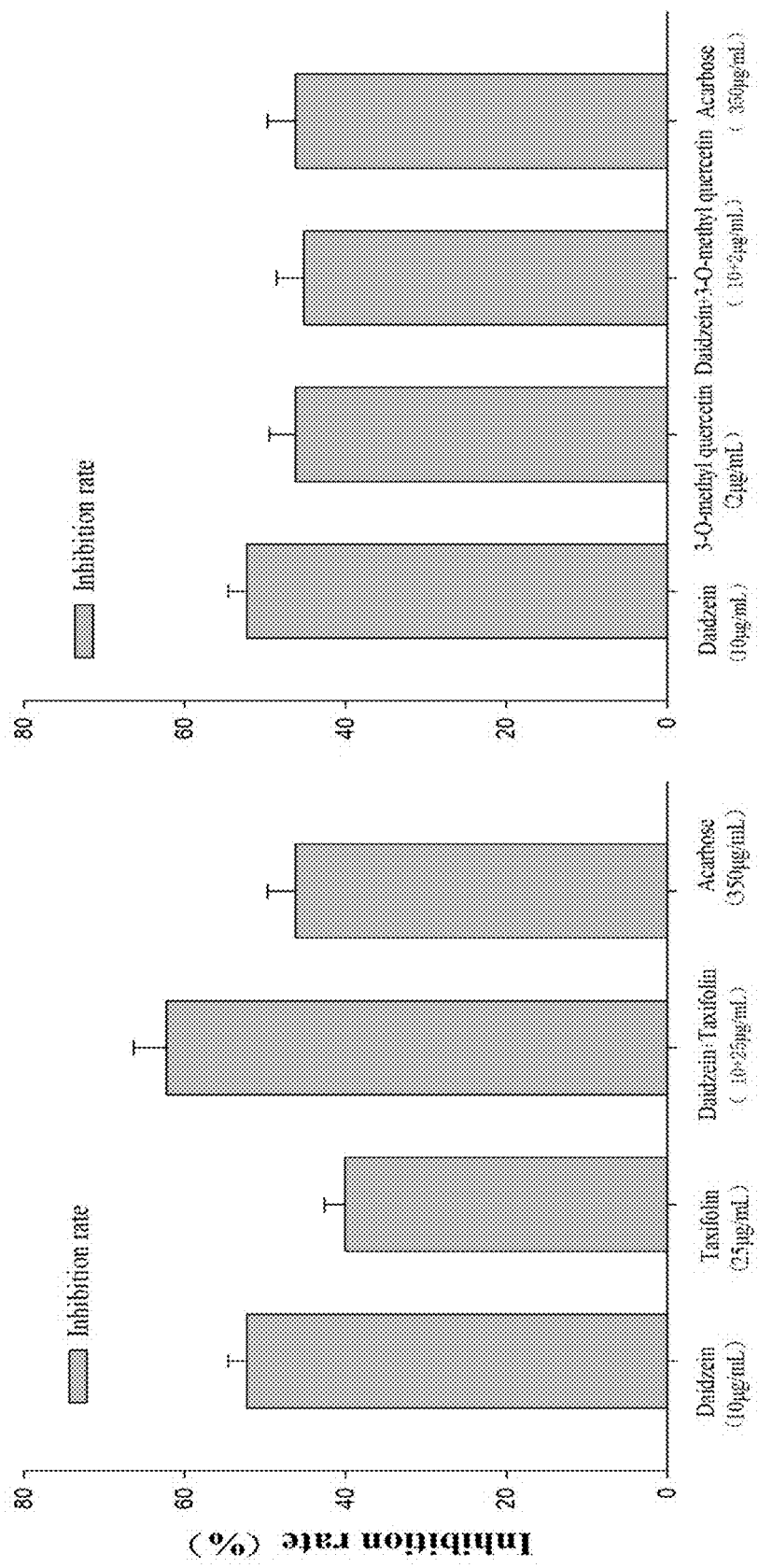
FIG. 12 is an inhibitory activity of daidzein compositions of Example 4 and Example 8 on α-glucosidase.

4. Inhibitory Activity of Daidzein Compositions of Example 4 and Example 8 on α-Glucosidase The inhibitory activity of daidzein compositions of Example 4 and Example 8 on α-glucosidase is shown in FIG. 12: inhibition rates of 10 μg/mL daidzein, 25 μg/mL taxifolin, 2 μg/mL 3-O-methyl quercetin and 350 μg/mL acarbose at the corresponding mass concentrations on α-glucosidase are 52.25±2.5%, 40.12±2.1%, 46.23±1.2%, 46.25±3.5% respectively; the inhibition rates of the daidzein and taxifolin composition (10+25 μg/mL) is 62.3±1.7%, and the inhibition rates of the daidzein and 3-O-methyl quercetin (10+2 μg/mL) is 45.2±2.5%. The results show that the composition does not significantly improve the inhibitory activity on α-glucosidase when used in combination.

Figure 13:
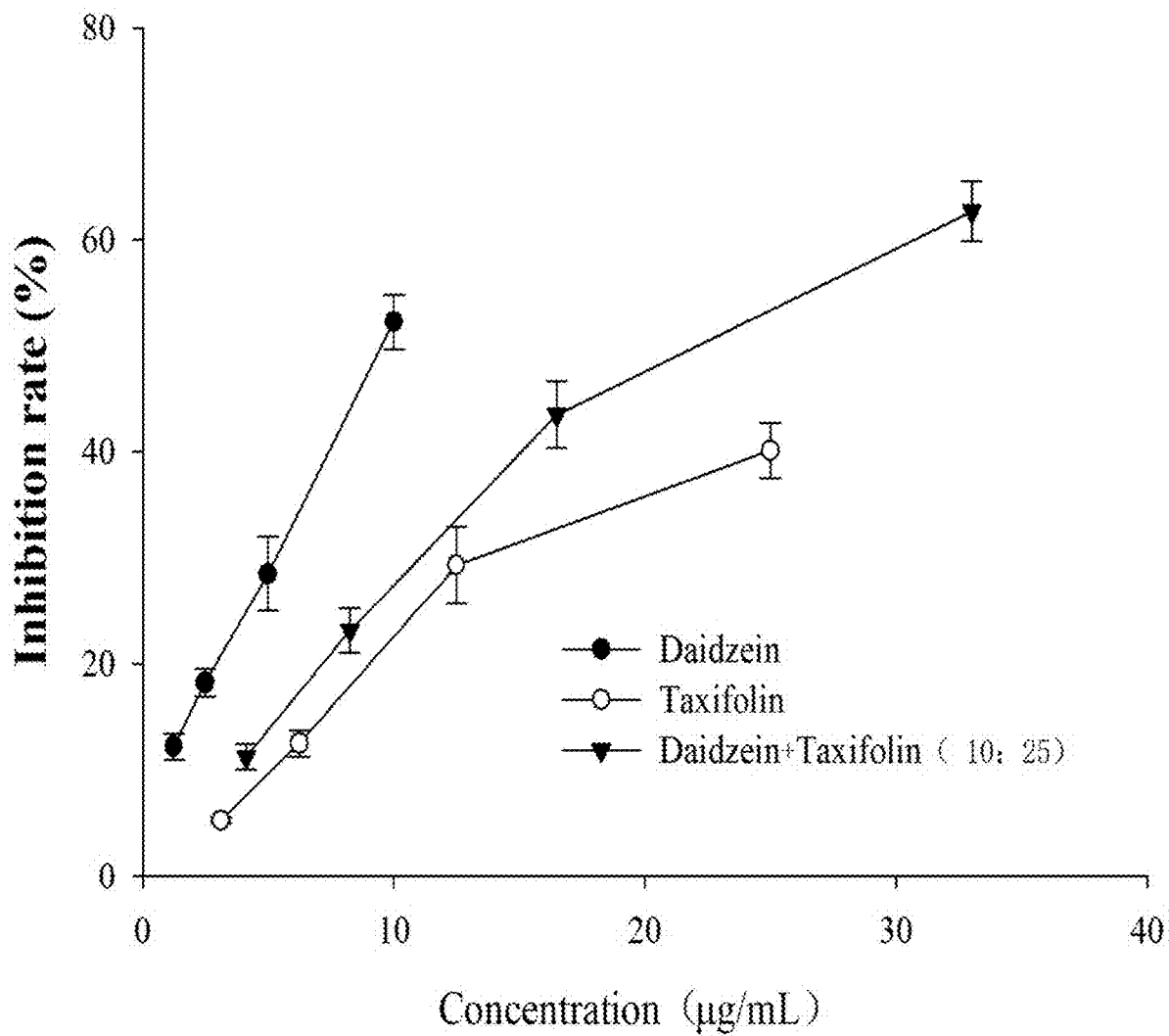
FIG. 13 is an inhibition curve graph of α-glucosidase by a daidzein+taxifolin (10:25) composition.

The α-glucosidase inhibitory activity of the daidzein and taxifolin composition at a mass ratio of 10:25 is tested at different concentration gradients, and the concentration gradient of the daidzein and taxifolin composition is (μg/mL): 10+25, 5+12.5, 2.5+6.25, 1.25+3.125; the concentration gradient of the daidzein is (μg/mL): 10, 5, 2.5, 1.25; the concentration gradient of the taxifolin is (μg/mL): 25, 12.5, 6.25, 3.125; and the results are shown in FIG. 13.

Figure 14:
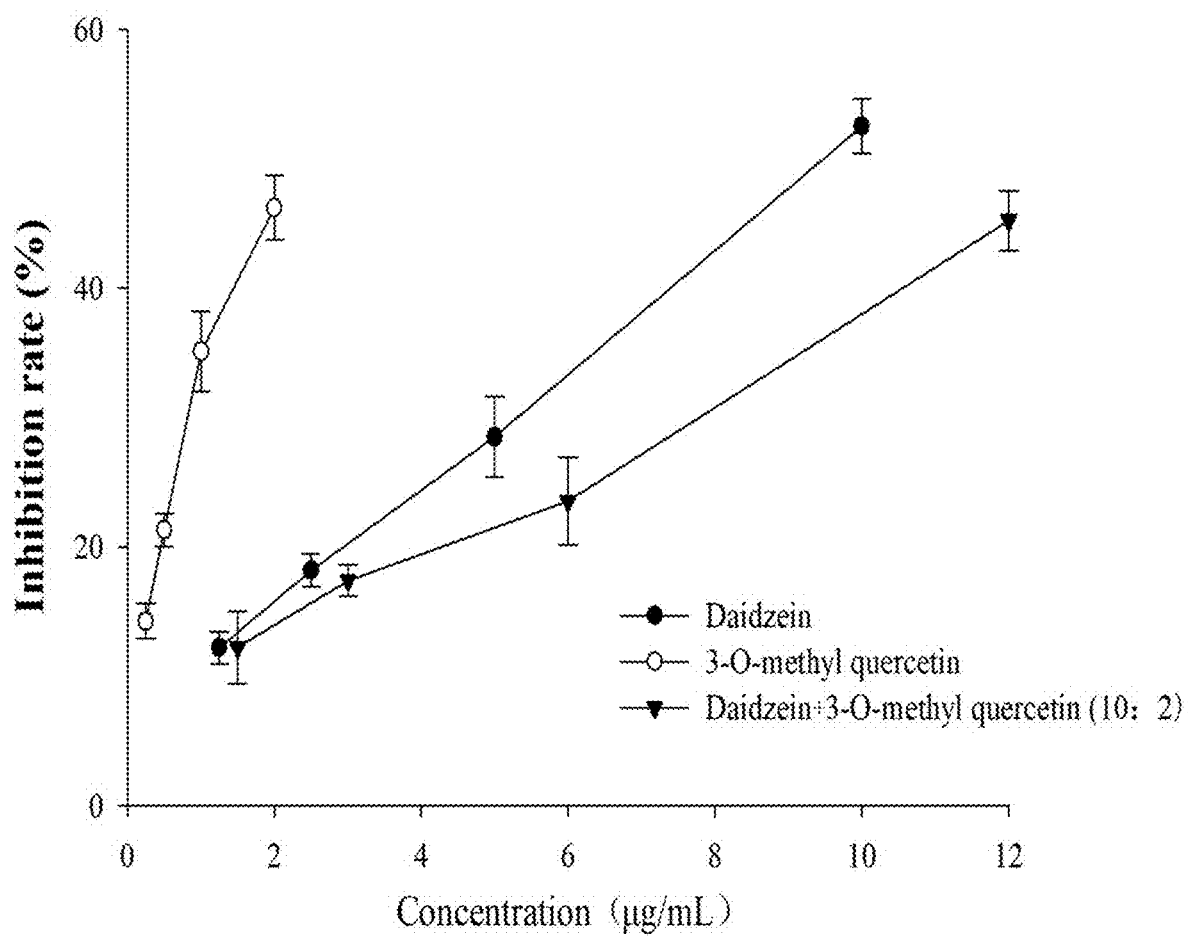
FIG. 14 is an inhibition curve graph of α-glucosidase by a daidzein+3-O-methyl quercetin (10:2) composition.

The α-glucosidase inhibitory activity of the daidzein and 3-O-methyl quercetin composition at a mass ratio of 10:2 is tested at different concentration gradients, and the concentration gradient of the daidzein and 3-O-methyl quercetin composition is (μg/mL): 10+2, 5+1, 2.5+0.5, 1.25+0.25; the concentration gradient of the daidzein is (μg/mL): 10, 5, 2.5, 1.25; the concentration gradient of the 3-O-methyl quercetin is (μg/mL): 2, 1, 0.5, 0.25; and the results are shown in FIG. 14.

The combination index (CI) of the daidzein composition of Example 4 and Example 8 is shown in Table 4:

TABLE 4

| Combination index (CI) of the daidzein composition of Example 4 and Example 8 | | | | | |
|---|---|---|---|---|---|
| Compound | Mass ratio | CI | | | |
| | | $GI_{50}$ | $GI_{75}$ | $GI_{90}$ | $CI_{avg}$ |
| Daidzein + taxifolin | 10:25 | 1.1 ± 0.02 | 1.0 ± 0.01 | 0.90 ± 0.03 | 0.97 |
| Daidzein + 3-O-methyl quercetin | 10:2 | >1 | >1 | >1 | >1 |

Data comes from results of three independent experiments and is represented as average value±standard difference From the results in Table 4, it can be seen that a combination of the daidzein and taxifolin (10:25) improves inhibitory activity on α-glucosidase, while a combination of the daidzein and 3-O-methyl quercetin (10:2) composition has no significant effect; when the combination of the daidzein and taxifolin (10:25) is used, the combination index (CI) is close to 1, showing a weak synergistic effect, and when the combination of the daidzein and 3-O-methyl quercetin (10:2) composition is used, the combination index (CI) is greater than 1, showing an antagonistic effect.

Comparative Example 1

This example demonstrates that the combination of each monomeric compound and daidzein does not have a synergistic effect. Each monomeric compound is selected from kaempferide, kaempferol, diosmetin, herbacetin, myricetin, morin, genkwanin, baicalein, hesperetin, fisetin, chrysin, epigallocatechin gallate, delphinidin, cyanidin, isoliquiritigenin, formononetin, and biochanin A.

First, the inhibition rates of various monomeric compounds under corresponding concentrations on the α-glucosidase are tested according to the above method, as shown in the following Table 5:

TABLE 5

| Monomer compound | Mass concentration (μg/mL) | Inhibition rate |
|---|---|---|
| Daidzein | 8 | 44.5 ± 2.5% |
| Kaempferide | 5 | 30.8 ± 1.3% |
| Kaempferol | 2.5 | 40.83 ± 2.3% |
| Diosmetin | 100 | 43.0 ± 2.1% |
| Herbacetin | 2.5 | 35.2 ± 1.2% |
| Myricetin | 1 | 41.2 ± 1.5% |
| Morin | 1 | 41.2 ± 2.7% |
| Genkwanin | 35 | 70.12 ± 5.5% |
| Baicalein | 10 | 38.8 ± 3.3% |
| Hesperetin | 30 | 45.2 ± 3.2% |
| Fisetin | 6 | 46.5 ± 2.3% |
| Chrysin | 100 | 51.2 ± 5.5% |
| Epigallocatechin gallate | 0.06 | 42.5 ± 3.5% |
| Delphinidin | 1 | 50.2 ± 4.3% |
| Cyanidin | 0.7 | 47.5 ± 1.4% |
| Isoliquiritigenin | 4 | 35.2 ± 2.5% |
| Formononetin | 20 | 60.07 ± 5.3% |
| Biochanin A | 0.7 | 38.5 ± 2.1% |

Then, each monomeric compound is combined with the daidzein, and the α-glucosidase inhibition rate of the composition is measured, as shown in the following Table 6:

TABLE 6

| Monomer compound | Monomer compound | Mass concentration ratio | Inhibition rate |
|---|---|---|---|
| | | 8:5 | 34.5 ± 1.3% |

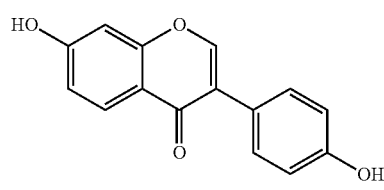

Daidzein

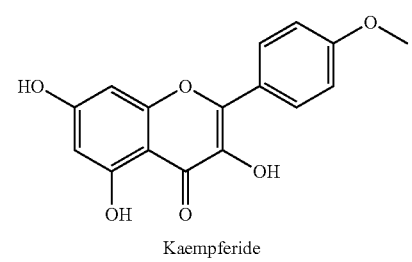 [SMILES: COc1ccc(-c2oc3cc(O)cc(O)c3c(=O)c2O)cc1]

Kaempferide

TABLE 6-continued
| Monomer compound | Monomer compound | Mass concentration ratio | Inhibition rate |
|---|---|---|---|
| | 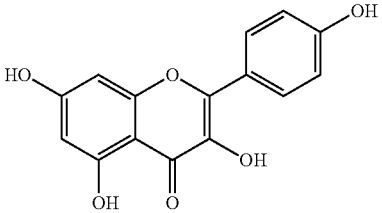 Kaempferol | 8:2.5 | 45.1 ± 2.8% |
| | 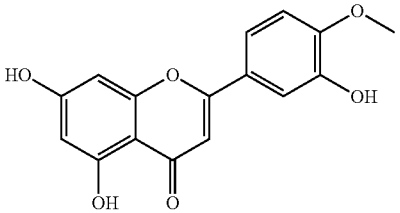 Diosmetin | 8:12 | 46.3 ± 3.7% |
| | 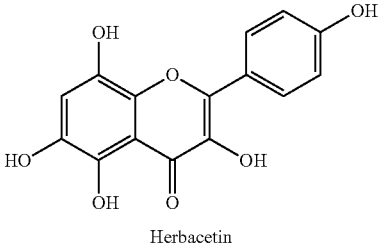 [SMILES: O=c1c(O)c(-c2ccc(O)cc2)oc2c(O)cc(O)c(O)c12] Herbacetin | 8:2.5 | 31.8 ± 1.8% |
| | 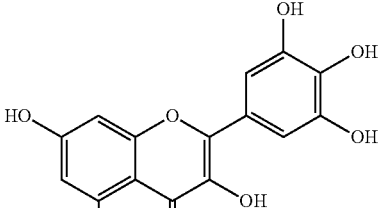 Myricetin | 8:1 | 17.4 ± 2.3% |
| | 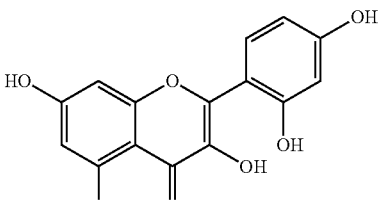 Morin | 8:1 | 38.5 ± 2.1% |

TABLE 6-continued
| Monomer compound | Monomer compound | Mass concentration ratio | Inhibition rate |
|---|---|---|---|
| | 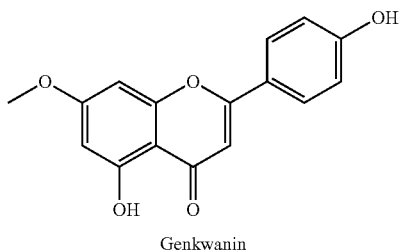 [SMILES: COc1cc(O)c2c(=O)cc(-c3ccc(O)cc3)oc2c1]<br>Genkwanin | 8:35 | 28.5 ± 1.5% |
| | 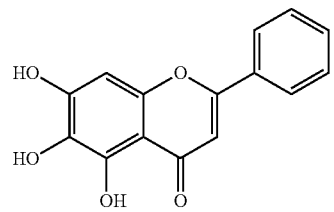<br>Baicalein | 8:10 | 38.3 ± 2.5% |
| | 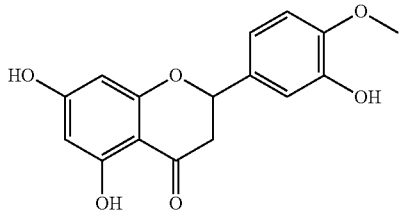<br>Hesperetin | 8:30 | 38.1 ± 2.3% |
| | 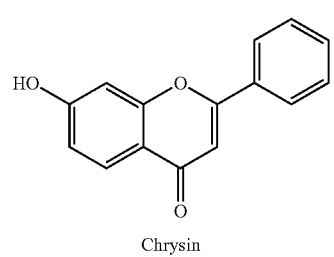 [SMILES: O=c1cc(-c2ccccc2)oc2cc(O)ccc12]<br>Chrysin | 8:100 | 24.7 ± 1.2% |
| | 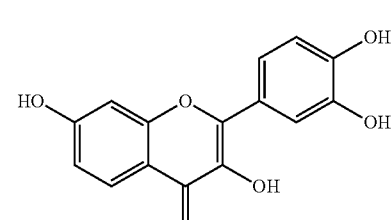<br>Fisetin | 8:6 | 28.3 ± 1.5% |

TABLE 6-continued
| Monomer compound | Monomer compound | Mass concentration ratio | Inhibition rate |
|---|---|---|---|
| | 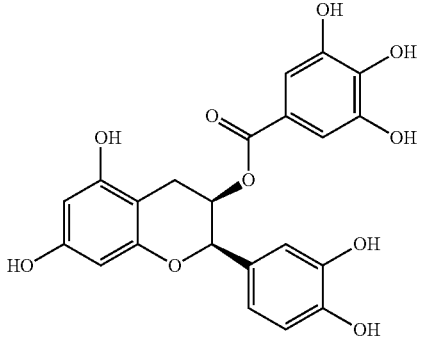 Epigallocatechin gallate | 8:0.06 | 34.5 ± 2.3% |
| | 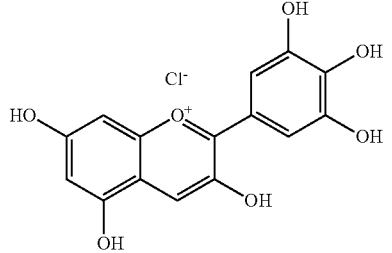 Delphinidin | 8:1 | 35.5 ± 2.6% |
| | 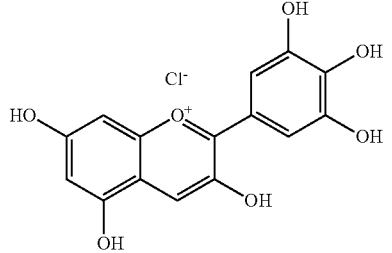 Cyanidin | 8:0.7 | 25.7 ± 2.3% |
| | 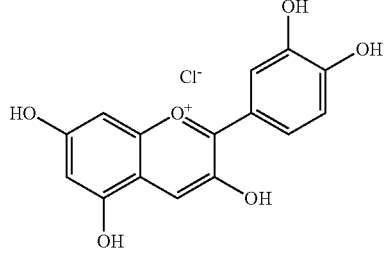 Isoliquiritigenin | 8:4 | 37.3 ± 1.5% |
| | 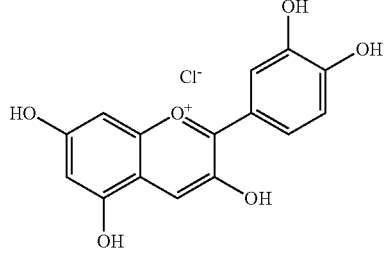 Formononetin | 8:20 | 51.2 ± 2.4% |

TABLE 6-continued

| Monomer compound | Monomer compound | Mass concentration ratio | Inhibition rate |
|---|---|---|---|
| | 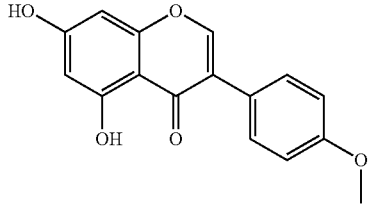Biochanin A | 8:0.7 | 42.6 ± 3.1% |

It can be seen from the Table 6 that after each monomeric compound is combined with the daidzein, the inhibition rate of composition thereof is directly lower than effect inhibition rate of a single compound, and the composition actually shows an antagonistic effect without a synergistic effect.

Comparative Example 2

This example demonstrates that the combination of each monomeric compound and 3-O-methyl quercetin does not have a synergistic effect. Each monomeric compound is selected from kaempferol, luteolin, vincetoxicoside B, herbacetin, myricetin, dihydromorin, vitexin, baicalein, taxifolin, hesperetin, chrysin, epigallocatechin gallate, delphinidin, cyanidin, isoliquiritigenin, phloretin, and biochanin A.

First, the inhibition rates of various monomeric compounds under corresponding concentrations on the α-glucosidase are tested according to the above method, as shown in the following Table 7:

TABLE 7

| Monomer compound | Mass concentration (μg/mL) | Inhibition rate |
|---|---|---|
| 3-Omethyl quercetin | 2 | 46.23 ± 1.2% |
| Kaempferol | 2.5 | 40.83 ± 2.3% |

TABLE 7-continued

| Monomer compound | Mass concentration (μg/mL) | Inhibition rate |
|---|---|---|
| Luteolin | 1 | 45.5 ± 2.7% |
| Vincetoxicoside | 12 | 48.7 ± 2.1% |
| Herbacetin | 2.5 | 35.2 ± 1.2% |
| Myricetin | 1 | 41.2 ± 1.5% |
| Dihydromorin | 15 | 25.7 ± 4.7% |
| Vitexin | 10 | 29.2 ± 1.4% |
| Baicalein | 10 | 38.8 ± 3.3% |
| Taxifolin | 25 | 40.12 ± 2.1% |
| Hesperetin | 30 | 45.2 ± 3.2% |
| Chrysin | 100 | 51.2 ± 5.5% |
| Epigallocatechin gallate | 0.06 | 42.5 ± 3.5% |
| Delphinidin | 1 | 50.2 ± 4.3% |
| Cyanidin | 0.7 | 47.5 ± 1.4% |
| Isoliquiritigenin | 4 | 35.2 ± 2.5% |
| Phloretin | 8 | 46.3 ± 2.7% |
| Biochanin A | 0.7 | 38.5 ± 2.1% |

Then, each monomeric compound is combined with the 3-O-methyl quercetin, and the α-glucosidase inhibition rate of the composition is measured, as shown in the following Table 8:

TABLE 8

| Monomer compound | Monomer compound | Mass concentration ratio | Inhibition rate |
|---|---|---|---|
| 3-O-methyl quercetin | | 2:2.5 | 44.25 ± 2.5% |

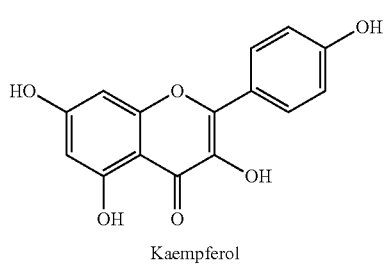 [SMILES: O=c1c(O)c(-c2ccc(O)cc2)oc2cc(O)cc(O)c12]
Kaempferol

TABLE 8-continued
| Monomer compound | Monomer compound | Mass concentration ratio | Inhibition rate |
|---|---|---|---|
| | 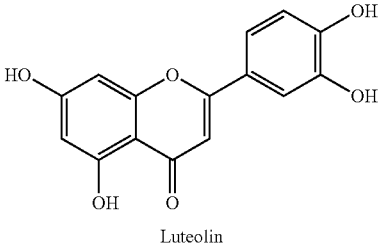 [SMILES: O=c1cc(-c2ccc(O)c(O)c2)oc2cc(O)cc(O)c12] Luteolin | 2:1 | 25.5 ± 3.2% |
| | 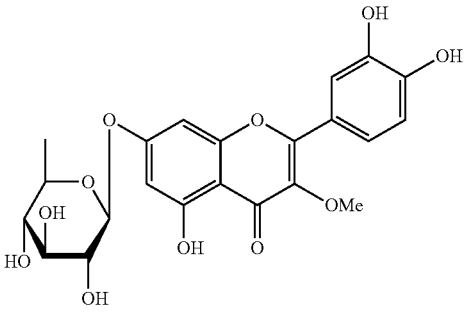 Vincetoxicoside | 2:12 | 42.3 ± 3.7% |
| | 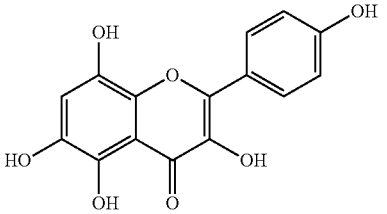 Herbacetin | 2:2.5 | 42.5 ± 1.8% |
| | 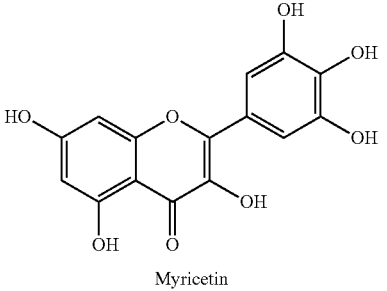 [SMILES: O=c1c(O)c(-c2cc(O)c(O)c(O)c2)oc2cc(O)cc(O)c12] Myricetin | 2:1 | 40.3 ± 2.3% |
| | 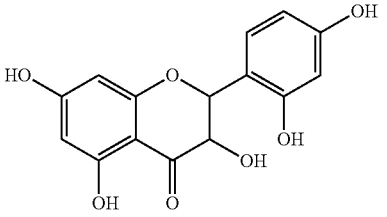 Dihydromorin | 2:15 | 43.5 ± 1.8% |

TABLE 8-continued
| Monomer compound | Monomer compound | Mass concentration ratio | Inhibition rate |
|---|---|---|---|
| | Vitexin 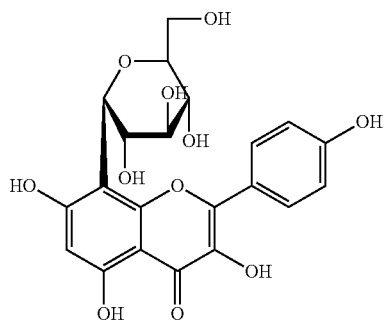 | 2:10 | 44.4 ± 1.5% |
| | Baicalein 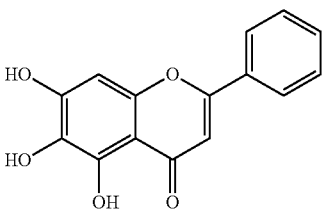 | 2:10 | 46.2 ± 2.3% |
| | Taxifolin 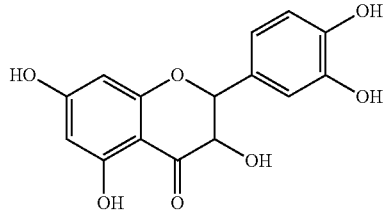 | 2:25 | 44.3 ± 4.9% |
| | Hesperetin 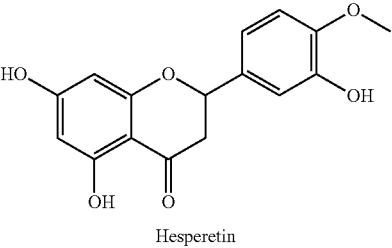 [SMILES: COc1ccc(C2CC(=O)c3c(O)cc(O)cc3O2)cc1O] | 2:30 | 42.7 ± 3.3% |
| | Chrysin 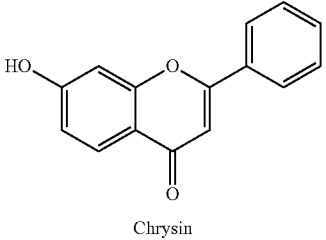 [SMILES: O=c1cc(-c2ccccc2)oc2cc(O)ccc12] | 2:100 | 45.4 ± 3.9% |

TABLE 8-continued
| Monomer compound | Monomer compound | Mass concentration ratio | Inhibition rate |
|---|---|---|---|
| | 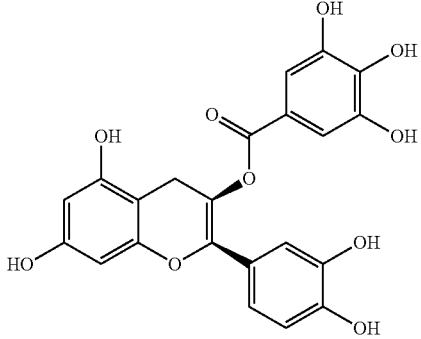<br>Epigallocatechin gallate | 2:0.06 | 42.5 ± 2.8% |
| | 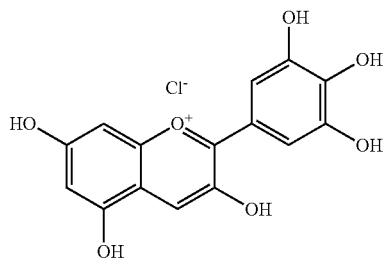<br>Delphinidin | 2:1 | 34.5 ± 3.1% |
| | 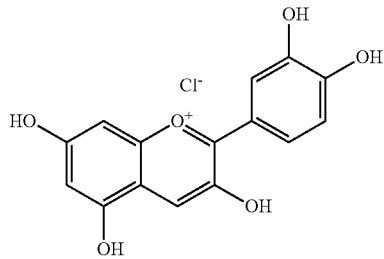<br>Cyanidin | 2:0.7 | 37.6 ± 3.6% |
| | 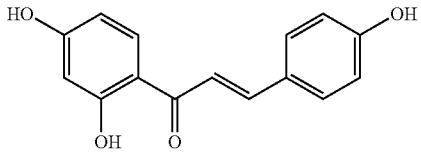<br>Isoliquiritigenin | 2:4 | 46.1 ± 1.5% |
| | 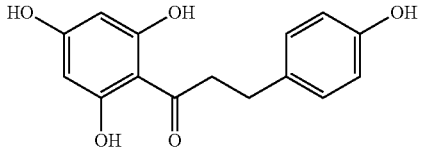<br>Phloretin | 2:8 | 43.2 ± 2.1% |

TABLE 8-continued

| Monomer compound | Monomer compound | Mass concentration ratio | Inhibition rate |
|---|---|---|---|
| | 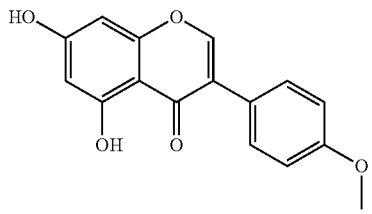Biochanin A | 2:0.7 | 45.2 ± 2.4% |

It can be seen from the Table 8 that after each monomeric compound is combined with the 3-O-methyl quercetin, the inhibition rate of composition thereof is directly lower than effect inhibition rate of a single compound, and the composition actually shows an antagonistic effect without a synergistic effect.

The above descriptions are only preferred embodiments of the present invention, and are not intended to limit the present invention in other forms. Any person familiar with the profession may use the technical content disclosed above to change or modify them into the equivalent embodiments of equivalent changes. However, any simple modification, equivalent change and modification made in accordance with the technical essence of the invention without departing from the technical solution of the invention are still within the scope of protection of the technical solutions of the invention.

What is claimed is:

1. A composition comprising a daidzein and a quercetin derivative, wherein the quercetin derivative is a taxifolin or a 3-O-methyl quercetin,
   wherein a mass ratio of the daidzein to the taxifolin is 8:25-10:25; and a mass ratio of the daidzein to the 3-O-methyl quercetin is 8:2-8:4.

2. A method of preparing a formulation having an effect of inhibiting α-glucosidase comprising: applying the composition of claim 1 to prepare the formulation.

3. An α-glucosidase inhibitor comprising a daidzein and a taxifolin; or a daidzein and a 3-O-methyl quercetin, as effective components,
   wherein a mass ratio of the daidzein to the taxifolin is 8:25-10:25; and a mass ratio of the daidzein to the 3-O-methyl quercetin is 8:2-8:4.

4. A method of preparing a drug having a hypoglycemic effect comprising:
   applying the composition of claim 1 to prepare the drug.

5. The method according to claim 4, wherein the hypoglycemic effect is to block digestion and absorption of carbohydrates by inhibiting activity of α-glucosidase to control postprandial hyperglycemia.

6. A medicine having a hypoglycemic effect comprising a daidzein and a taxifolin; or a daidzein and a 3-O-methyl quercetin, as effective components,
   wherein a mass ratio of the daidzein to the taxifolin is 8:25-10:25; and a mass ratio of the daidzein to the 3-O-methyl quercetin is 8:2-8:4.

7. The medicine according to claim 6, wherein the medicine further comprises a carrier, a solvent, a diluent, and an excipient.

8. The medicine according to claim 6, wherein a dosage form of the medicine is selected from the group consisting of powder, granule, capsule, injection, oral liquid, and tablet.

* * * * *